(12) United States Patent
Kipke et al.

(10) Patent No.: US 9,907,475 B2
(45) Date of Patent: Mar. 6, 2018

(54) IMPLANTABLE MICRO-COMPONENT ELECTRODES

(75) Inventors: Daryl R. Kipke, Dexter, MI (US); Takashi Daniel Yoshida Kozai, Pittsburgh, PA (US); Nick Langhals, Haslett, MI (US); Joerg Lahann, Ann Arbor, MI (US); Nicholas A. Kotov, Ypsilanti, MI (US); Xiaopei Deng, Ann Arbor, MI (US); Paras Patel, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 1375 days.

(21) Appl. No.: 13/805,132

(22) PCT Filed: Jun. 16, 2011

(86) PCT No.: PCT/US2011/040741
§ 371 (c)(1),
(2), (4) Date: Dec. 18, 2012

(87) PCT Pub. No.: WO2011/159923
PCT Pub. Date: Dec. 22, 2011

(65) Prior Publication Data
US 2013/0090542 A1  Apr. 11, 2013

Related U.S. Application Data

(60) Provisional application No. 61/356,482, filed on Jun. 18, 2010.

(51) Int. Cl.
*A61B 5/04* (2006.01)
*A61N 1/00* (2006.01)
(Continued)

(52) U.S. Cl.
CPC .......... *A61B 5/04001* (2013.01); *A61B 5/685* (2013.01); *A61N 1/05* (2013.01);
(Continued)

(58) Field of Classification Search
CPC .. A61N 1/0551; A61N 1/0529; A61N 1/0531; A61N 1/0534; A61N 1/0565;
(Continued)

(56) References Cited

U.S. PATENT DOCUMENTS

| | | | |
|---|---|---|---|
| 5,215,088 A * | 6/1993 | Normann | A61B 5/04001 600/377 |
| 7,596,415 B2 * | 9/2009 | Brabec | A61N 1/056 600/372 |

(Continued)

OTHER PUBLICATIONS

International Search Report and Written Opinion of the ISA, ISA/KR, dated Feb. 29, 2012 in corresponding International Patent Application No. PCT/US2011/040741 (7 pages).

*Primary Examiner* — Joseph Stoklosa
*Assistant Examiner* — Brian M Antiskay
(74) *Attorney, Agent, or Firm* — Harness, Dickey & Pierce, P.L.C.

(57) ABSTRACT

The present disclosure provides robust implantable micro-component electrodes that can be used in a variety of medical devices. The medical device may be a neural probe that can monitor or stimulate neural activity in an organism's brain, spine, nerves, or organs, for example. The micro-component electrode has a small physical profile, with ultra-thin dimensions, while having high strength and flexibility. The micro-electrode has an electrically conductive core material, e.g., carbon. The surface of the core material includes one or more electrically conductive regions coated with an electrically conductive material and one or more non-conductive regions having an electrically non-conductive biocompatible polymeric coating. Implantable devices having such micro-components are capable of implantation in an organism for very long durations.

22 Claims, 23 Drawing Sheets

Figure 1A:
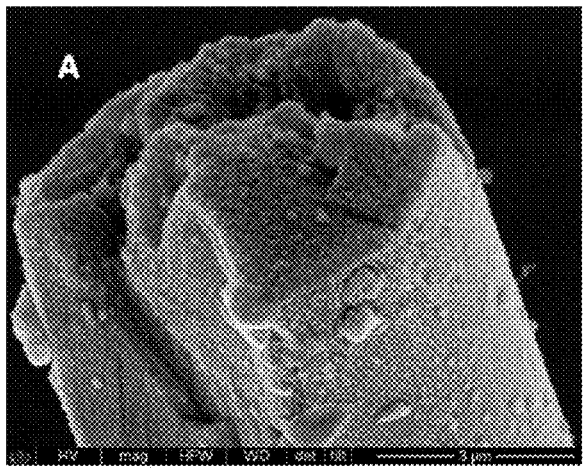

(51) Int. Cl.
  *A61B 5/00* (2006.01)
  *A61N 1/05* (2006.01)
  *B82Y 5/00* (2011.01)
(52) U.S. Cl.
  CPC ......... *A61N 1/0529* (2013.01); *A61N 1/0551* (2013.01); *A61B 2562/125* (2013.01); *B82Y 5/00* (2013.01)
(58) Field of Classification Search
  CPC .... A61N 1/36103; A61N 1/04; A61N 1/0539; A61N 1/0456; A61N 1/36025; A61N 1/3606; A61N 1/36114; A61N 1/36182; A61B 5/04001; A61B 5/0478; A61B 5/06
  USPC ........ 600/372–373, 377–379, 393, 544–545; 607/115–118
  See application file for complete search history.

(56) References Cited

U.S. PATENT DOCUMENTS

| | | | |
|---|---|---|---|
| 7,844,347 B2* | 11/2010 | Brabec | A61N 1/0556 600/372 |
| 8,489,203 B2* | 7/2013 | Ortmann | A61B 5/04001 600/377 |
| 2003/0100823 A1* | 5/2003 | Kipke | A61B 5/04001 600/378 |
| 2004/0111141 A1* | 6/2004 | Brabec | A61N 1/0556 607/119 |
| 2005/0021117 A1* | 1/2005 | He | A61N 1/0529 607/116 |
| 2005/0143790 A1* | 6/2005 | Kipke | A61B 5/04001 607/60 |
| 2006/0276866 A1 | 12/2006 | McCreery | |
| 2007/0060815 A1 | 3/2007 | Martin et al. | |
| 2008/0140195 A1 | 6/2008 | Su et al. | |
| 2008/0255439 A1 | 10/2008 | Tang et al. | |
| 2009/0043369 A1* | 2/2009 | Radeloff | A61N 1/0541 607/137 |
| 2009/0248113 A1* | 10/2009 | Nimer | A61N 1/05 607/60 |
| 2011/0087126 A1* | 4/2011 | Zorzos | A61B 5/0478 600/544 |
| 2011/0213193 A1* | 9/2011 | Nair | A61K 9/0009 600/9 |
| 2011/0288391 A1* | 11/2011 | Rao | A61B 5/04001 600/373 |

* cited by examiner

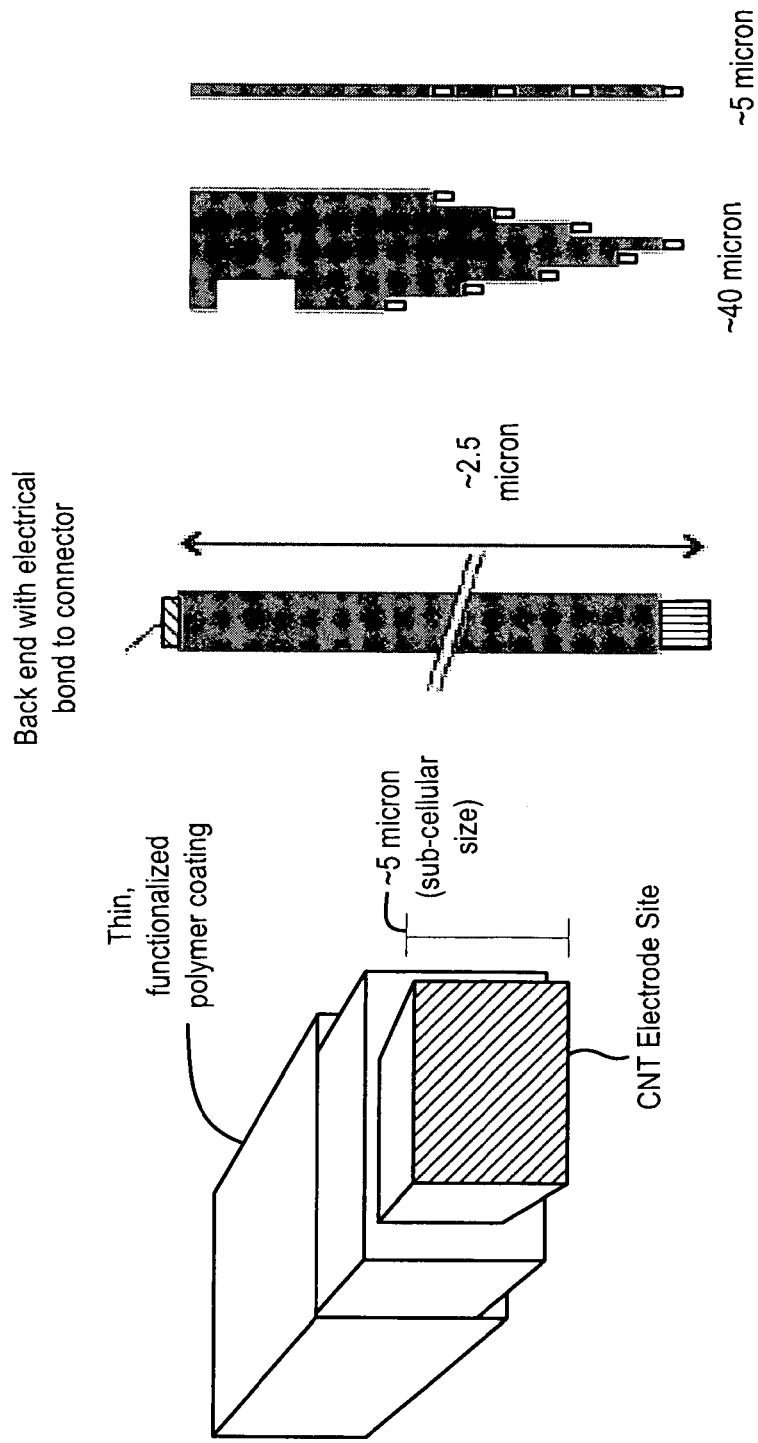

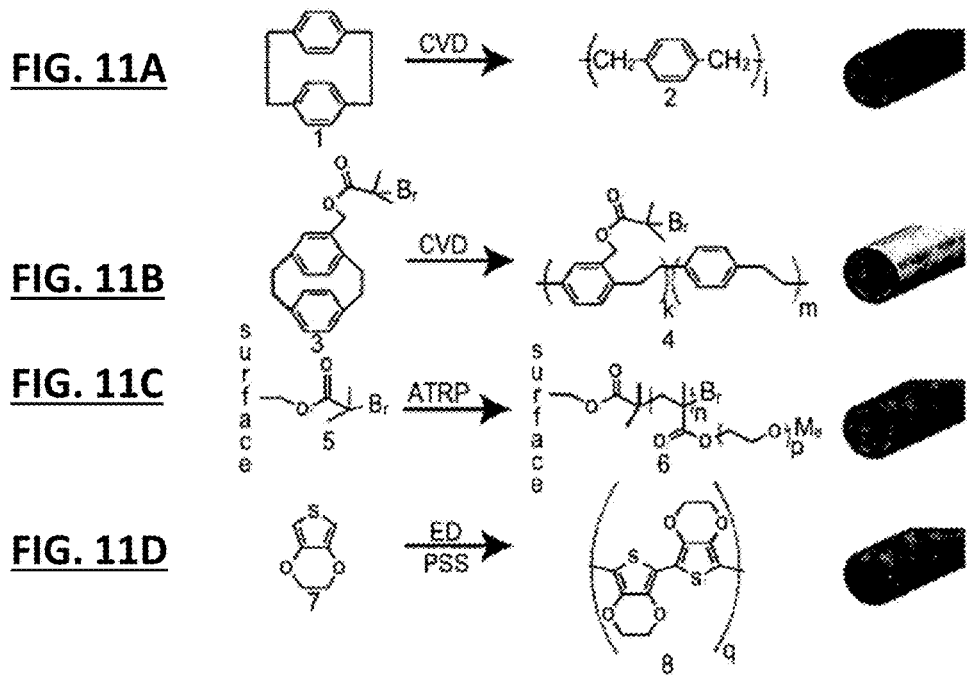
FIG. 11A
FIG. 11B
FIG. 11C
FIG. 11D
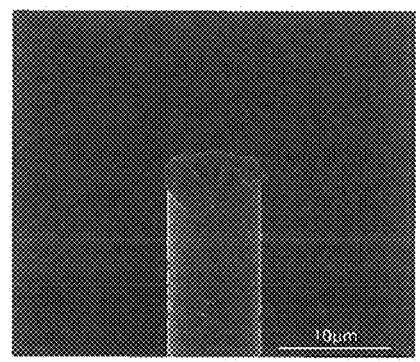
FIG. 11E
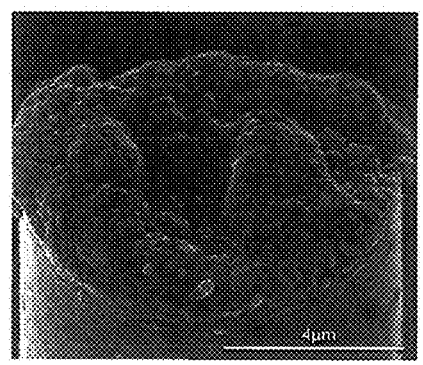
FIG. 11F

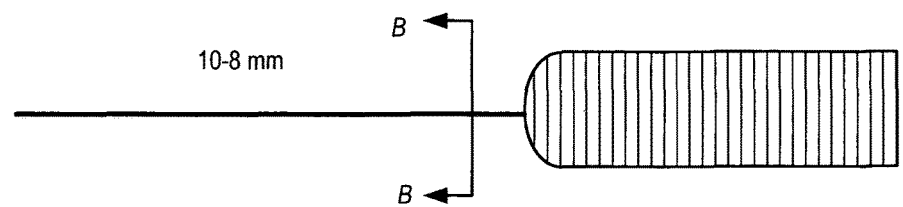
FIG. 12A
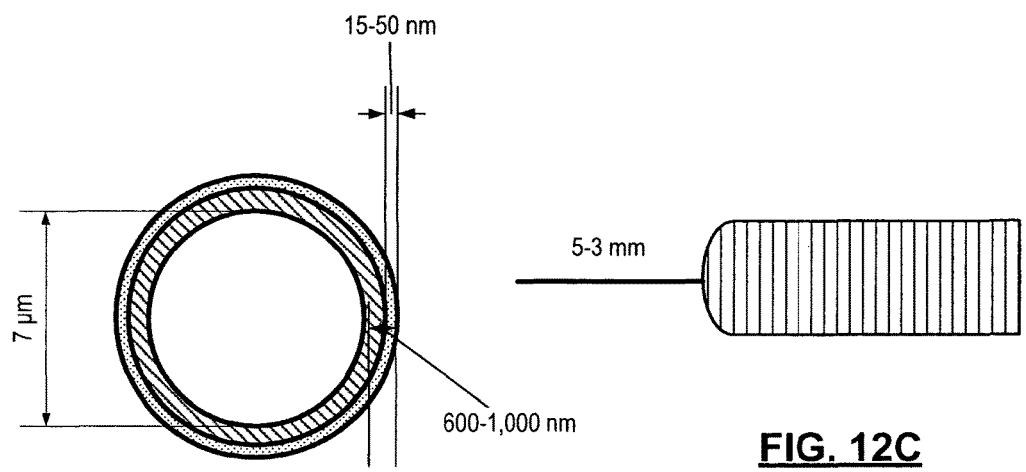
FIG. 12B
FIG. 12C
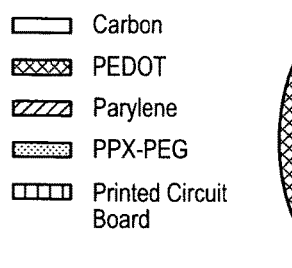
FIG. 12D

High Speed Recordings
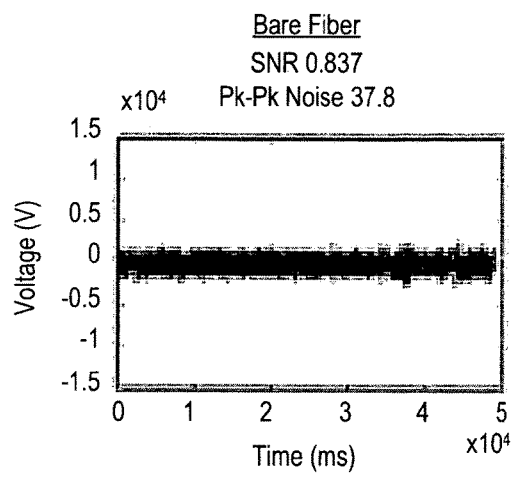
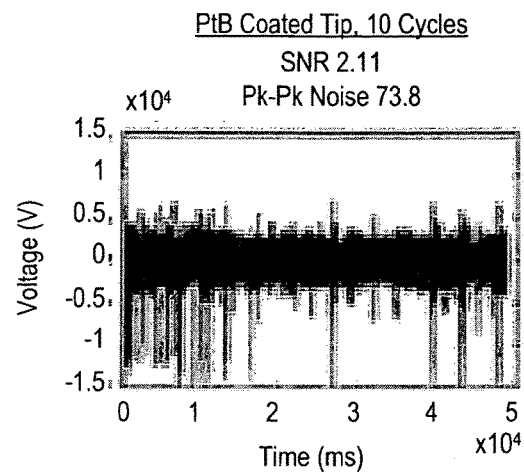
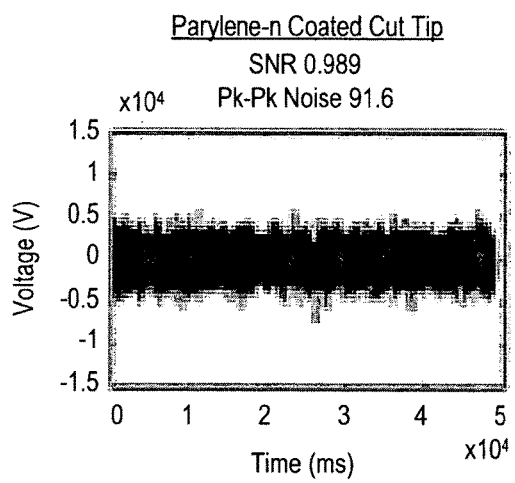
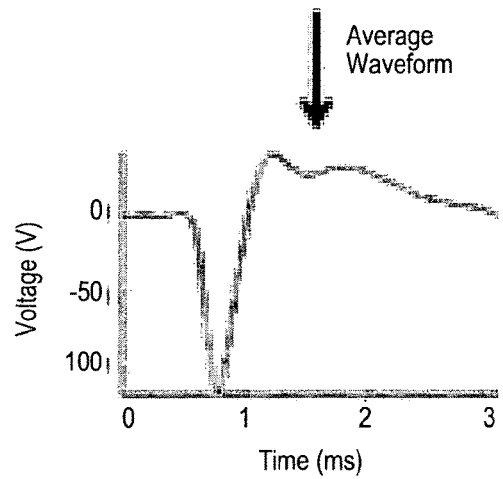
FIG. 13F

IMPLANTABLE MICRO-COMPONENT ELECTRODES

CROSS-REFERENCE TO RELATED APPLICATIONS

This application is a 371 U.S. National Stage of International Application No. PCT/US2011/040741, filed Jun. 16, 2011, which claims the benefit of U.S. Provisional Application No. 61/356,482, filed on Jun. 18, 2010. The entire disclosures of the above applications are incorporated herein by reference.

GOVERNMENT RIGHTS

This invention is made with government support under NS068396 and EB002030 awarded by the National Institutes of Health. The government has certain rights in the invention.

FIELD

The present disclosure relates to conductive micro-components, and more specifically to conductive micro-component electrodes capable of implantation in an organism to monitor electrophysiological and/or electrochemical activity, such as a neural probe for monitoring neural activity.

BACKGROUND

This section provides background information related to the present disclosure which is not necessarily prior art.

Implantable microscale neural probes are important tools for neuroscience. The capability of monitoring specific neuronal ensembles for long periods of time with great precision is a powerful tool in neuroscience research for linking low-level neuronal circuits to high-level brain function, such as learning, memory, and perception. On the clinical side, it also enables the development of closed-loop neurostimulation and neuroprosthetic systems using detailed neurophysiological signals for feedback. Beyond neural recording applications, such microelectrodes can enable new approaches for creating long-lasting, high-fidelity neural interfaces that would directly benefit neurostimulation applications.

Since the pioneering work of Strumisser in 1958 introducing microwire bundles for chronic neural recordings in hibernating squirrels, there has been an ongoing push to develop improved implantable microelectrode technologies. While various implantable probes have been investigated, the recording quality is not optimally high. Further, eventually the recordings degrade and ultimately fail over time with conventional implantable microelectrodes. The primary challenge in neural interface technologies today remains that of making reliable implantable devices for long-term, stable, high-fidelity spike recordings from selective neuronal ensembles.

SUMMARY

This section provides a general summary of the disclosure, and is not a comprehensive disclosure of its full scope or all of its features.

In various aspects, the present disclosure provides implantable micro-component electrodes. In certain aspects, the present disclosure pertains to an implantable micro-component electrode that comprises an electrically conductive core material. In certain aspects, the conductive core material may have an elastic tensile modulus of greater than or equal to about 200 GPa and a nominal value of stiffness of greater than or equal to about 5 GN/μm. In certain variations, the electrically conductive core material comprises carbon. Further, the implantable micro-component electrode comprises one or more electrically conductive regions disposed on the surface of the electrically conductive core material. The one or more electrically conductive regions comprise an electrically conductive biocompatible coating. Further, the implantable micro-component electrode comprises an electrically non-conductive biocompatible coating disposed on regions of the surface of the electrically conductive core material. The regions where the electrically non-conductive biocompatible coating is disposed are those where the one or more electrically conductive regions are absent. In various aspects, the micro-component electrode has at least one dimension of less than or equal to about 10 μm. In certain aspects, the electrically non-conductive biocompatible coating has a thickness of less than 1 μm.

In other aspects, the present teachings provide a micro-component electrode for an implantable medical device that comprises an electrically conductive core material comprising carbon and having a diameter of less than or equal to about 10 μm. One or more electrically conductive regions are disposed on the surface of the electrically conductive core material. The one or more electrically conductive regions comprise an electrically conductive polymeric coating. Further, an electrically non-conductive polymeric coating is disposed on regions of the surface of the electrically conductive core material where the one or more electrically conductive regions are absent. In certain variations, the electrically non-conductive coating comprises a parylene polymer or a parylene polymer derivative. In certain variations, the electrically conductive non-conductive coating has a thickness of less than or equal to about 1 μm.

In yet other aspects, the present disclosure provides methods of monitoring, sensing, or stimulating neural activity in an organism. In one aspect, such a method comprises electrically communicating with a probe implanted into an organism. In certain variations, the method comprises electrically communicating with a neural probe implanted into a brain of an organism. The probe optionally has a cross-sectional area of less than or equal to about 2,000 micrometers-squared (μm$^2$) and comprises at least one micro-component electrode. The at least one micro-component electrode comprises an electrically conductive core material having a surface with one or more electrically conductive regions disposed on the surface of the electrically conductive core material. The one or more electrically conductive regions disposed on the surface of the electrically conductive core comprise an electrically conductive polymeric coating. Further, an electrically non-conductive polymeric coating is disposed on regions of the surface of the electrically conductive core material corresponding to locations where the one or more electrically conductive regions are absent. In certain variations, the micro-component electrode has at least one dimension less than or equal to about 10 μm.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 1B:
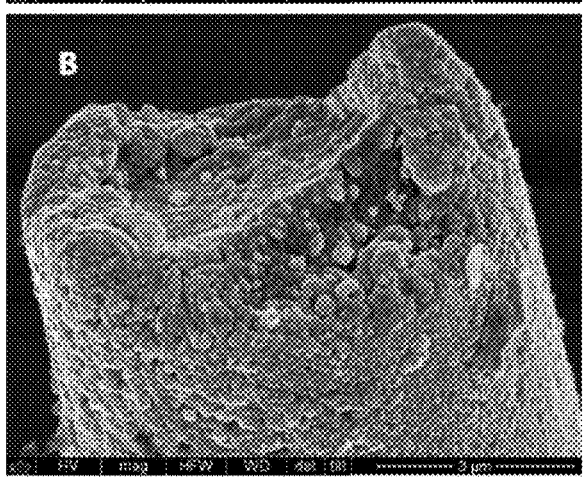
Figure 1C:
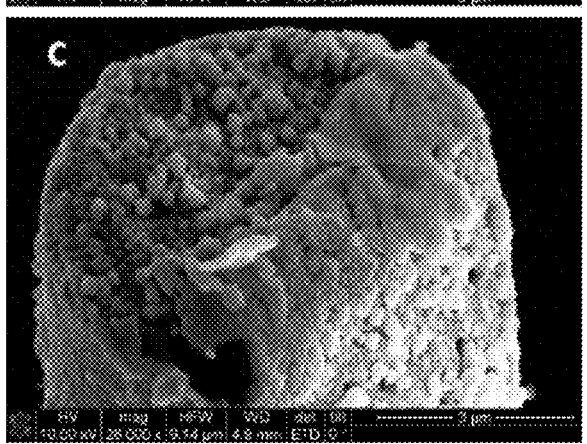
Figure 1D:
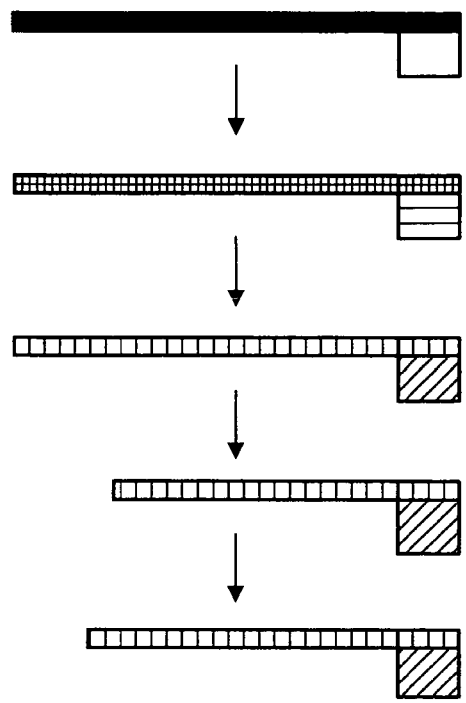
Figure 1E:
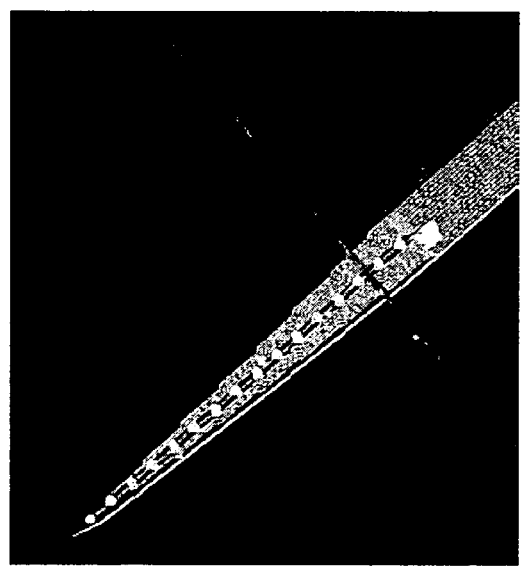

FIGS. 1A-1E show comparative performance of micro-component electrodes, some of which are prepared in accordance with the present teachings. FIGS. 1A-1C are scanning electron microscopy SEM images of comparative bare carbon fibers (1A), 800 nm parylene-N coated carbon fibers (1B), and parylene coated carbon fiber with an electrodeposited PEDOT/PSS electrode recording site (1C). FIG. 1D is an assembly of micro-component microthread electrodes (MTE); carbon fibers are mounted onto a print circuit board, chemical vapor deposition (CVD) parylene coated, functionalized parylene coated with poly(ethylene glycol) (PPX-PEG) coated, cut, and Poly(3,4-ethylenedioxythiophene) (PEDOT) electrodeposited. FIG. 1E is a size comparison of a 5 mm "Michigan" style electrode and a Microthread Electrode prepared with the micro-component electrodes of the present disclosure.

Figure 2A:
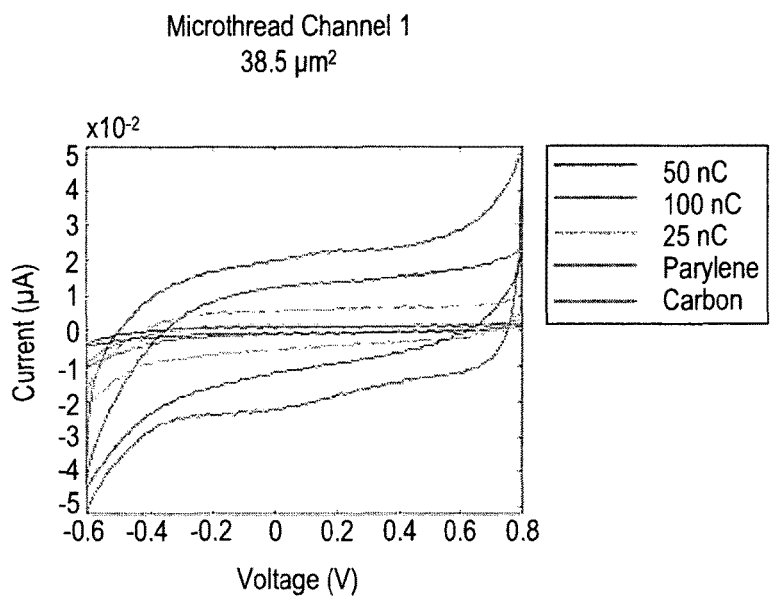
Figure 2B:
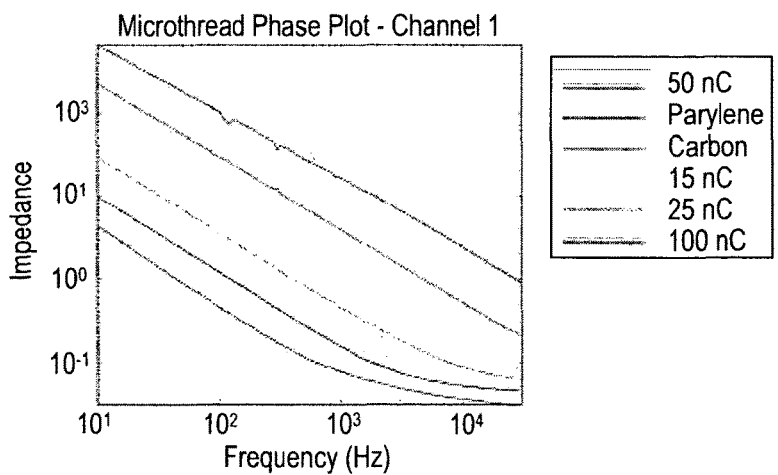
Figure 2C:
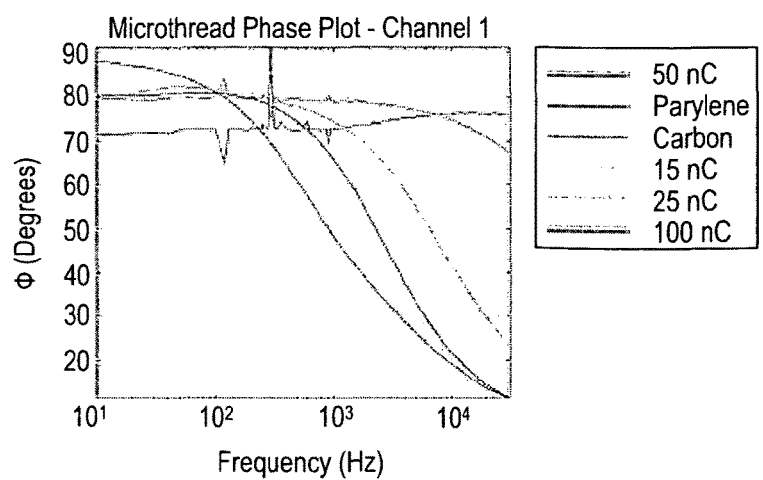
Figure 2D:
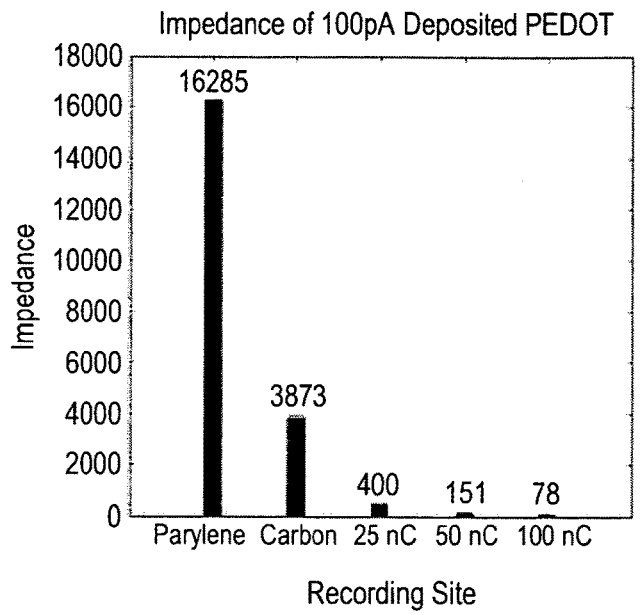

FIGS. 2A-2E show in vitro characterization of Microthread Electrodes. FIG. 2A is Cyclic Voltammetry traces (CV) of parylene coated fiber, parylene coated carbon fiber with an exposed carbon tip, and parylene coated carbon fiber with an electrodeposited PEDOT/PSS recording site using various deposition charge densities. FIG. 2B is a Bode magnitude impedance plot. FIG. 2C is a Bode phase plot. FIG. 2D is a comparison at 1 kHz impedance. And FIG. 1E is a comparison of charge carrying capacity.

Figure 3A:
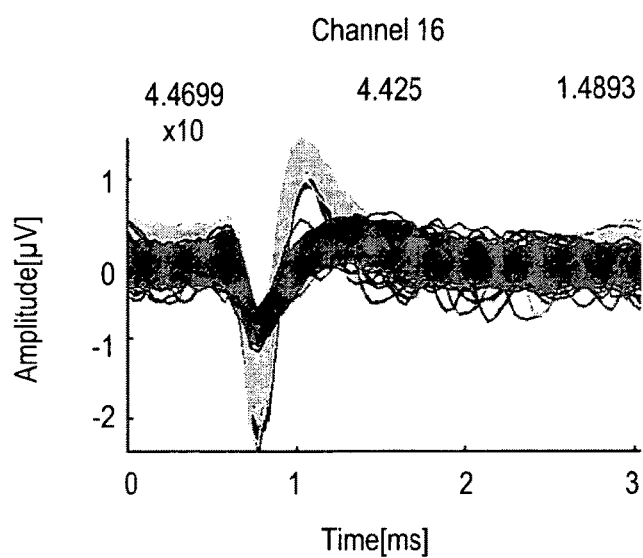
Figure 3B:
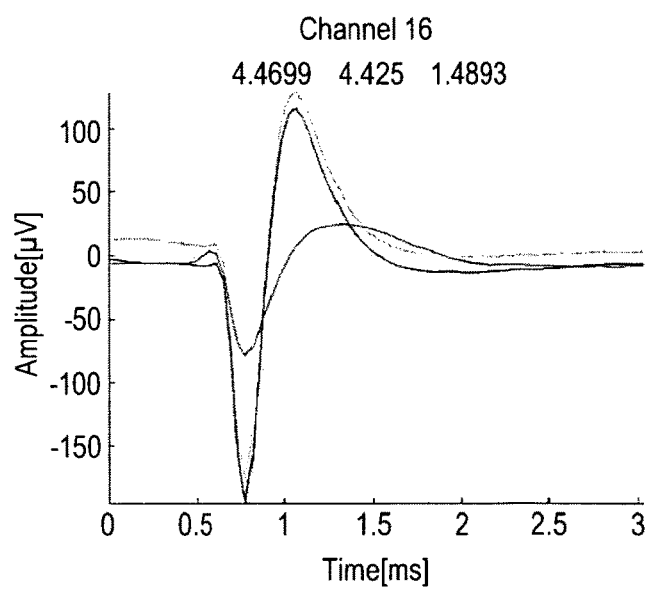
Figure 3C:
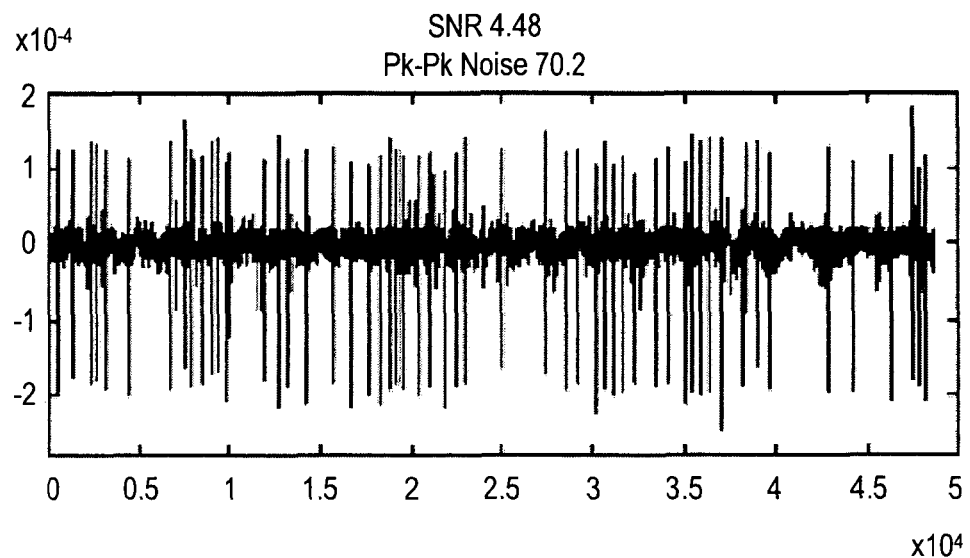
Figure 3D:
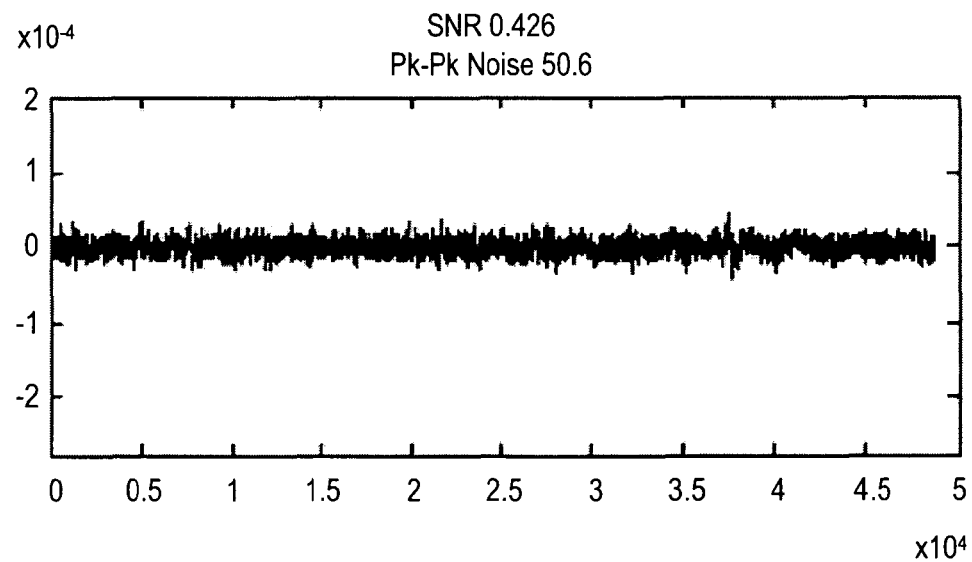
Figure 3E:
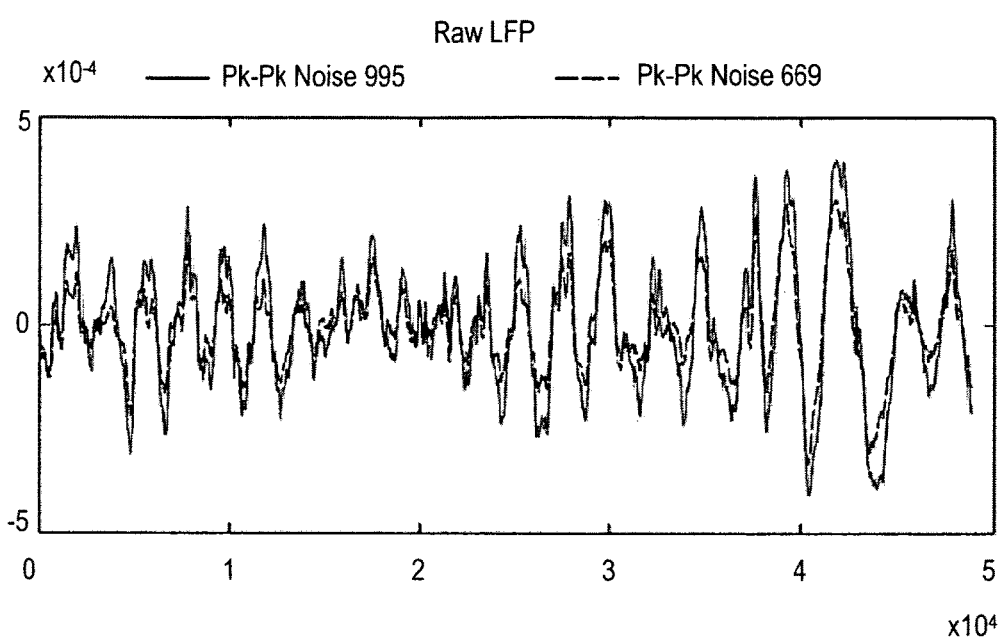

FIGS. 3A-3E show in vivo single unit recording capabilities of micro-component electrodes prepared in accordance with the present teachings. FIG. 3A is a piled single unit neural recordings from a parylene coated PEDOT microthread electrode. FIG. 3B is an average unit spike. FIGS. 3C and 3D are five seconds of raw neural recordings from a PEDOT site MTE (3C) and a comparative carbon site MTE (3D). FIG. 3E shows five seconds of Local Field Potential (LFP) recordings from a PEDOT site MTE and a comparative carbon site MTE (3E).

Figure 4A:
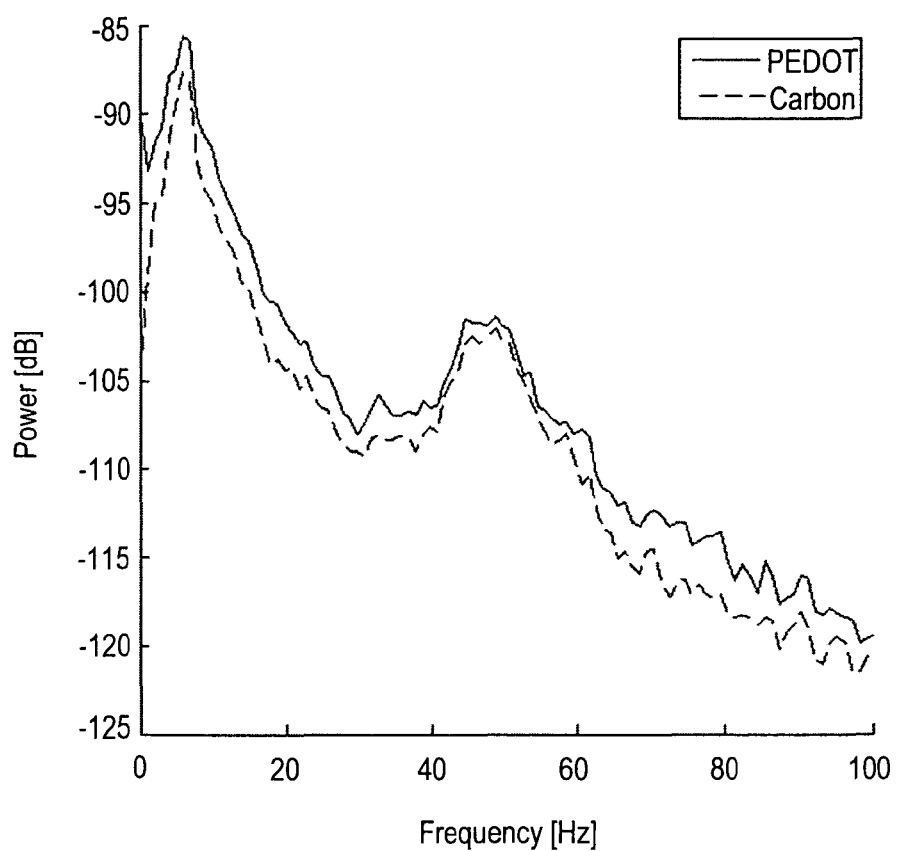
Figure 4B:
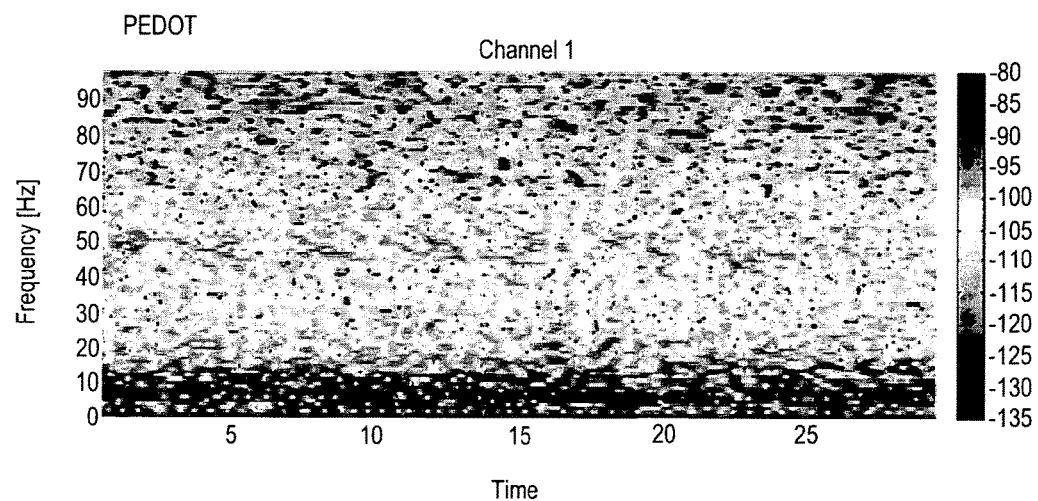
Figure 4C:
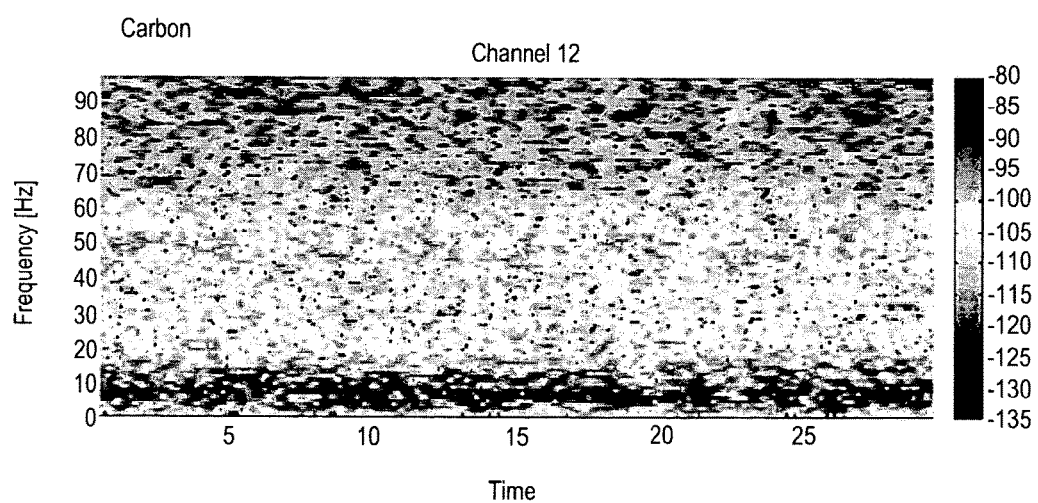

FIGS. 4A-4C show in vivo characterization of micro-component electrodes prepared in accordance with the present teachings. FIG. 4A show a Power Spectral Density plot of carbon site MTE and PEDOT site MTE (4A). FIGS. 4B and 4C show Spectrograms of comparative PEDOT site MTE (4B) and carbon site MTE (4C).

Figures 5A, 5B:
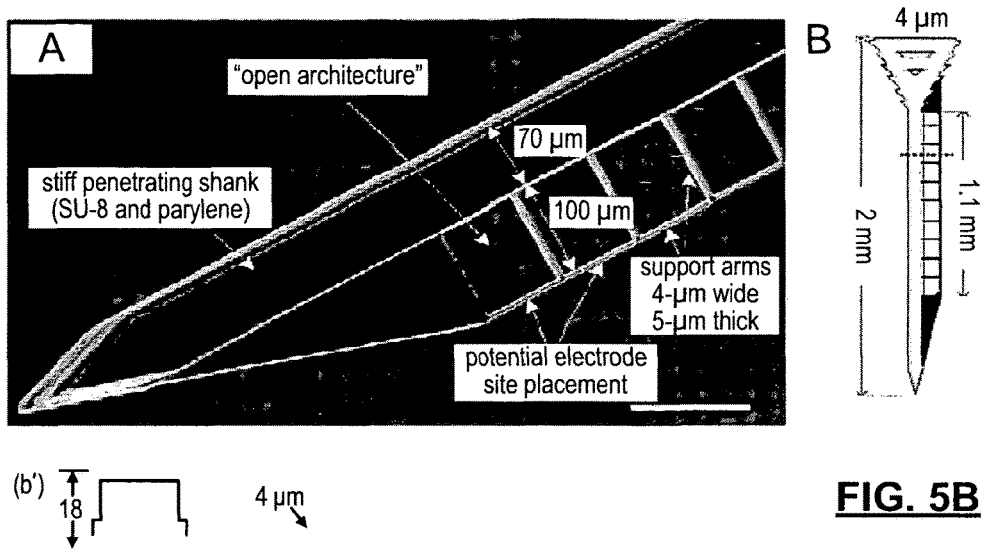

FIGS. 5A-5B' show a neural probe design with sub-cellular dimensions using a thin lateral platform. FIG. 5A is an SEM perspective view of a parylene-based open architecture device used for in vivo testing. The tip of the device is at the lower left. FIG. 5B is a CAD drawing of probe design indicating overall length and width of the lattice structures (4 µm), and FIG. 5B' is a cross-sectional view of line A-A' shown in (FIG. 5B). Scale of bars is 100 µm.

Figure 6A:
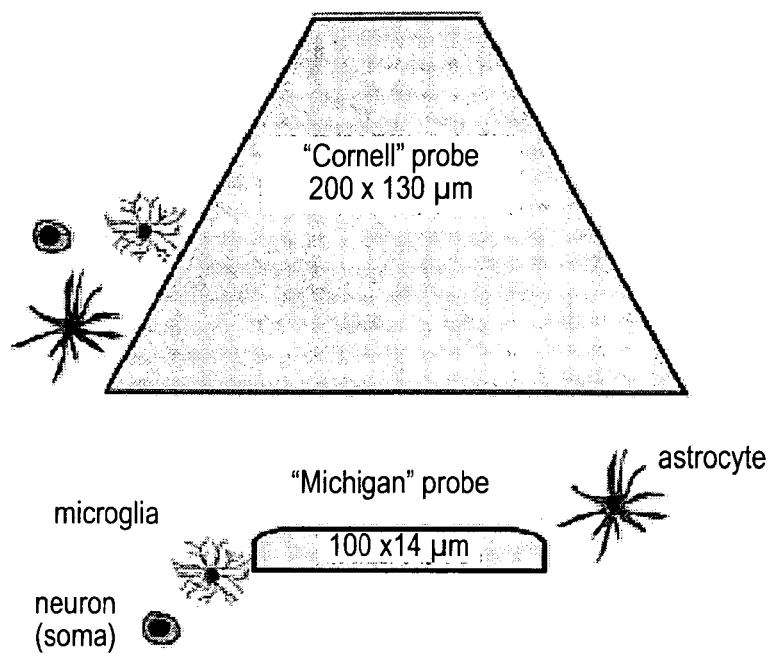
Figure 6B:
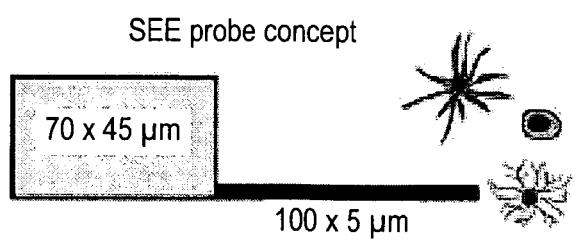

FIGS. 6A-6B are an illustration of the biomimetic principle of sub-cellular size to modulate a foreign body response. FIG. 6A has two structures having a similar tissue response after 4-weeks, but not having sub-cellular dimensions and FIG. 6B is a cross-section of a SEE probe. Each of FIGS. 6A-6C shows microglia, which are large relative to the 5 µm edge.

Figure 7A:
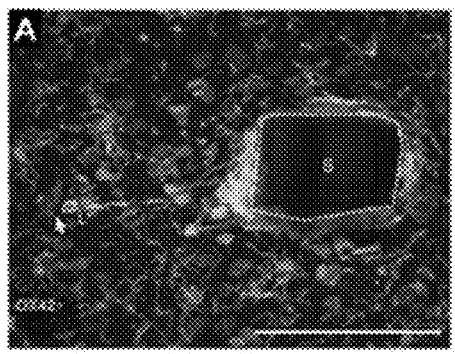
Figure 7B:
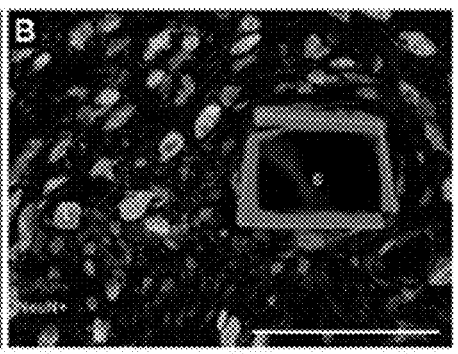
Figure 7C:
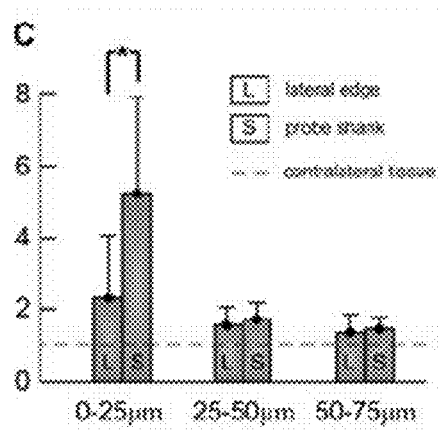
Figure 7D:
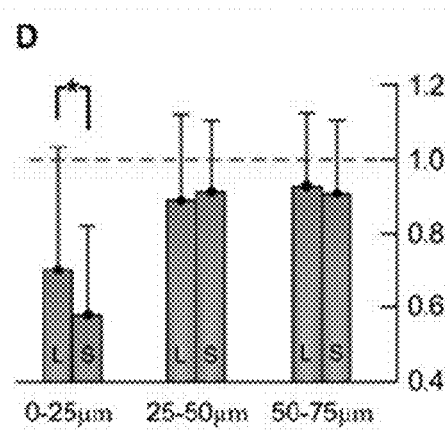

FIGS. 7A-7D show examples of qualitative and quantitative results around a non-functional probe. FIG. 7A shows GFAP and OX42 antibodies label astrocytes and microglia, respectively. FIG. 7B shows GFAP and NeuN labeling astrocytes and neuronal nuclei. FIG. 7C is normalized mean nonneuronal density as a functional of distance from probe interface and FIG. 7D is a mean neuronal density. P<0.05 and scale is 100 µm.

FIGS. 8A-8C shows diagrams of assemblies of micro-components prepared in accordance with the present disclosure. FIG. 8A shows a single-strand micro-component electrode. FIG. 8B shows a side profile sectional view of the single-strand micro-component electrode. FIG. 8B shows a multi-strand microthread probe illustrating the flexible carbon nanotube (CNT) composite core and electrode site with a thin, conformal coating of an insulating and functionalized polymer. The CNT is nominally 5 µm on a side and has a 0.5 to 1 µm thick coating to give the probe a sub-cellular dimension.

Figure 9:
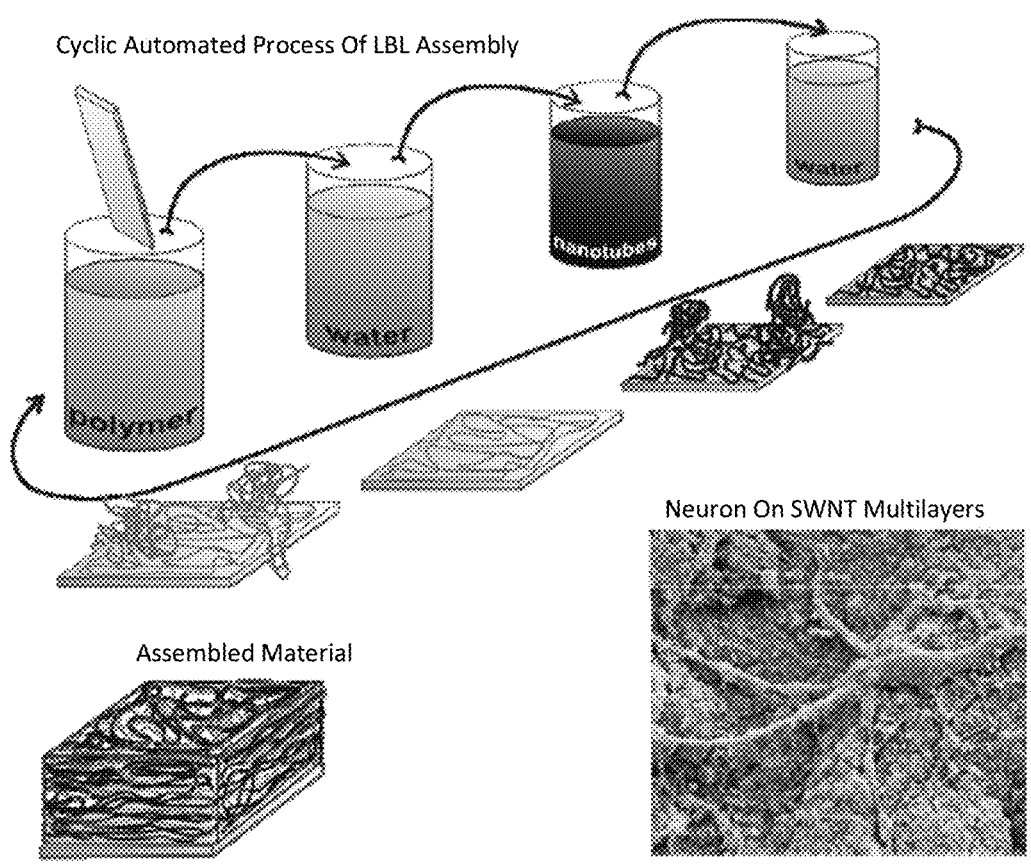

FIG. 9 is a schematic of the layer-by-layer assembly process that can be used to form core composite materials for the micro-components of the present disclosure. The inset shows an SEM micrograph of cultured neuron on SWNT multilayers.

Figure 10:
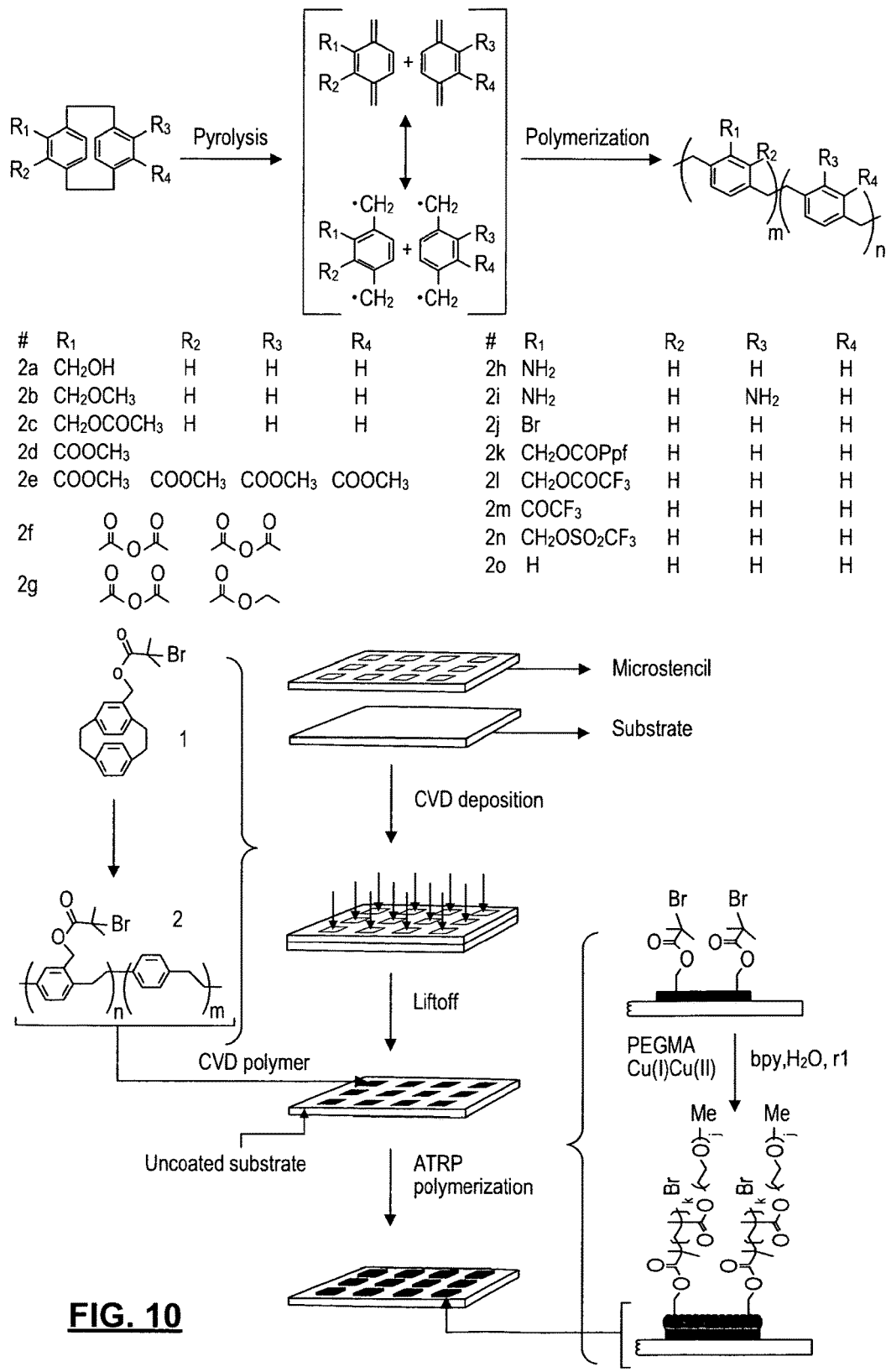

FIG. 10 shows CVD polymerization of various [2.2] paracyclophanes to create functionalized non-conductive parylene coatings on substrates for use in conjunction with the present teachings. Corresponding reference numerals indicate corresponding parts throughout the several views of the drawings. The lower portion of the drawing shows spatially controlled CVD deposition.

FIGS. 11A-11F shows an exemplary formation of parylene coating and functionalizing polymeric coatings by atom-transfer radical polymerization (ATRP) applied to a conductive core material to form a micro-component of the present disclosure. In FIG. 11A carbon fibers are coated with 800 nm poly(p-xylylene). In FIG. 11B, the fiber of FIG. 11A is further coated with a 50 nm layer of poly[(p-xylylene-4-methyl-2-bromoisobutyrate)-co-(p-xylylene)]. In FIG. 11C, poly(ethylene glycol) (PEG) is covalently grafted onto poly[(p-xylylene-4-methyl-2-bromoisobutyrate)-co-(p-xylylene)] through ATRP. FIG. 11D shows removal of insulation by cutting away the tip to expose a carbon site, and then electrodeposited with PEDOT. FIGS. 11E-11F are SEM images of such modified MTEs prepared in accordance with the present teachings.

FIGS. 12A-12D show exemplary schematics and cross section of architecture of a neural probe incorporating a micro-component electrode in accordance with one aspect of the present teachings. FIG. 12A shows a first side view of an exemplary neural probe. FIG. 12B shows a detailed sectional view taken along line B-B in FIG. 12A. FIG. 12C shows a second side view of another exemplary neural probe. FIG. 12D shows a detailed sectional view of the layers forming an exemplary MTE probe.

Figure 13A:
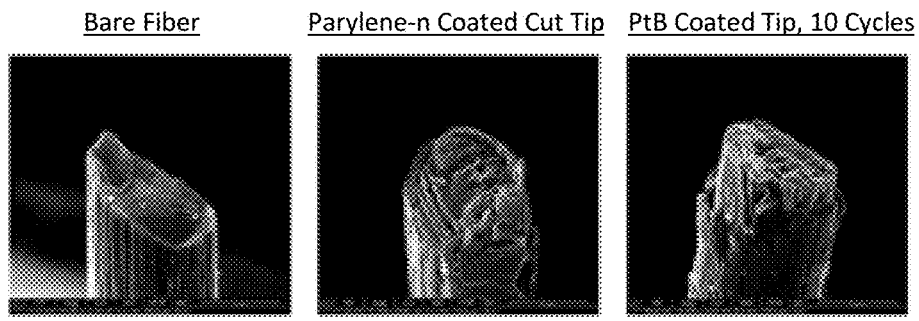
Figure 13B:
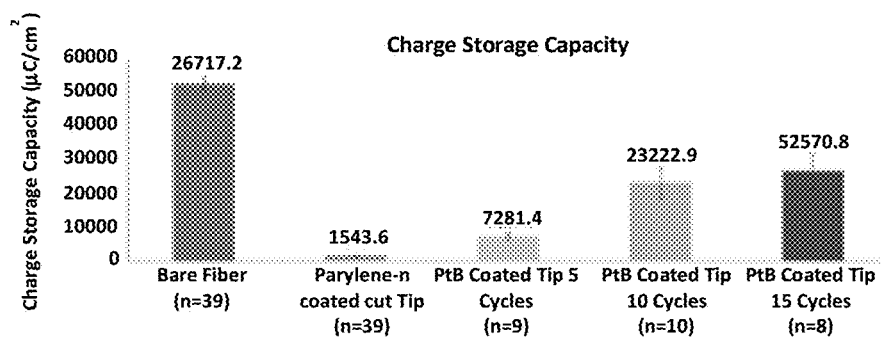
Figure 13C:
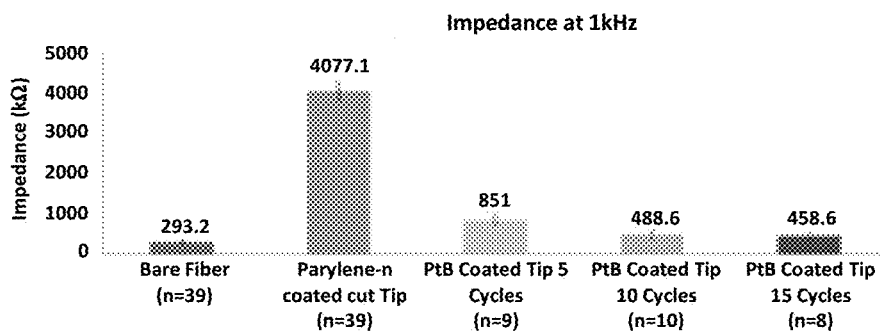
Figure 13D:
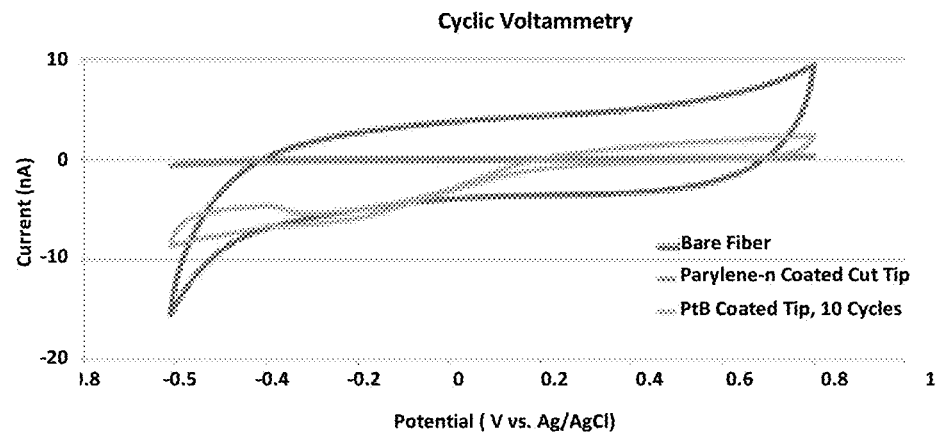
Figure 13E:
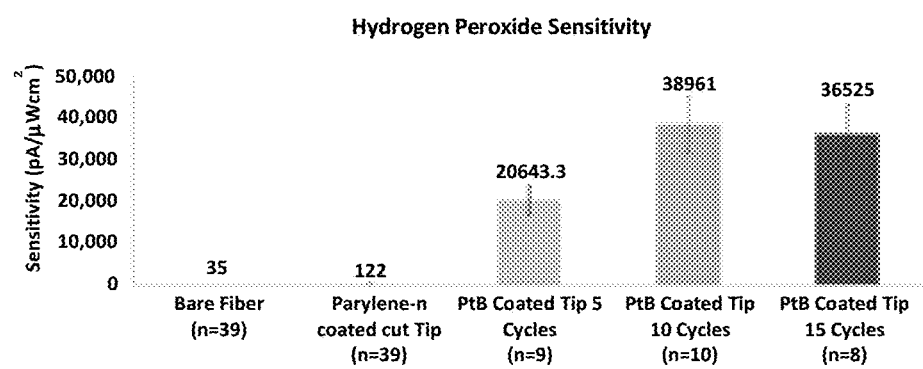

FIGS. 13A-13F. FIG. 13A shows scanning electron microscopy (SEM) images of comparative bare carbon fibers, 800 nm parylene-N coated carbon fiber with an exposed conductive carbon tip site, and parylene coated carbon fiber with an electrodeposited platinum black recording site. FIG. 13B show comparative charge storage capacity. FIG. 13C shows comparative 1 kHz impedance. FIG. 13D is cyclic voltammetry traces (CV) of bare carbon fibers, 800 nm parylene-N coated carbon fiber with an exposed conductive carbon tip site, and parylene coated carbon fiber with an electrodeposited platinum black recording site. FIG. 13E shows comparative electrochemical sensitivity to hydrogen peroxide during constant potential amperometry. FIG. 13F shows comparative performances of electrical recording capabilities.

Figure 14A:
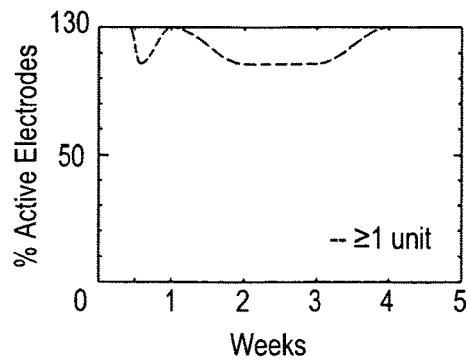
Figure 14B:
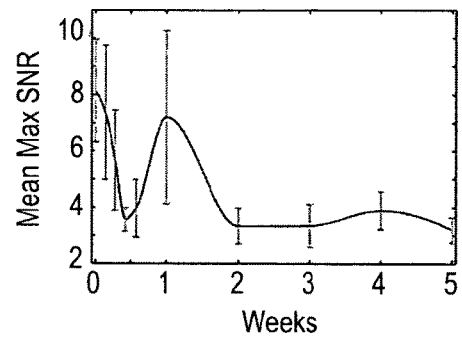
Figure 14C:
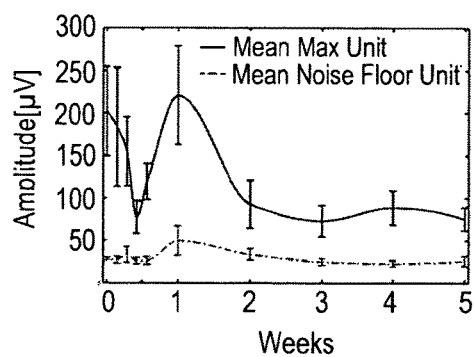
Figure 14D:
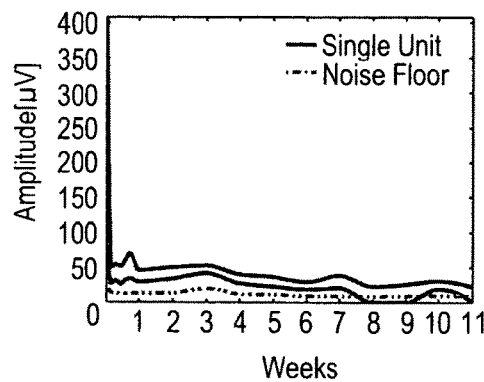
Figure 14E:
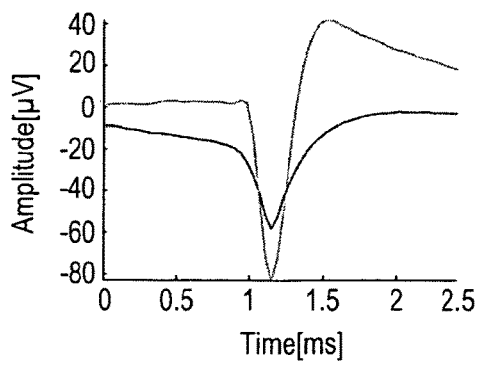
Figure 14F:
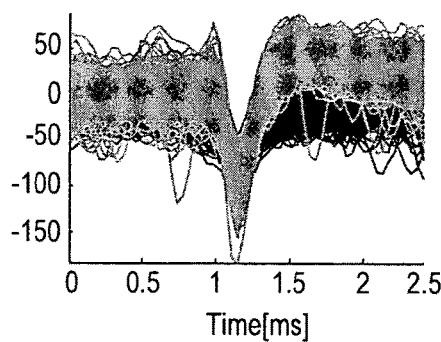
Figure 14G:
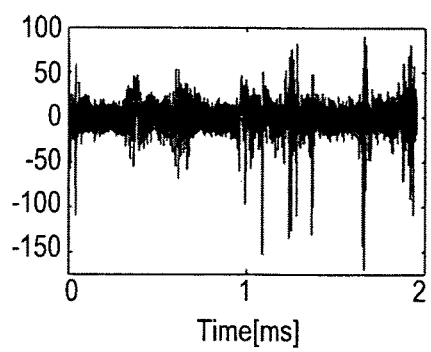
Figure 14H:
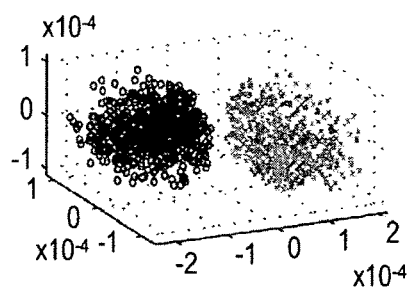
Figure 14I:
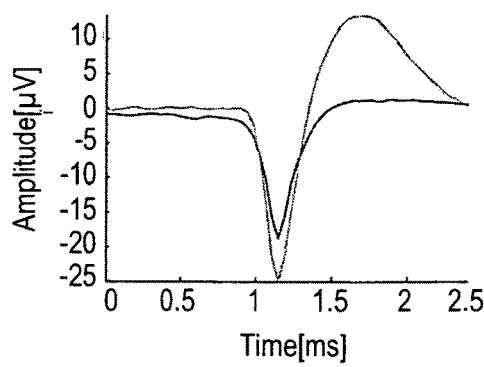
Figure 14J:
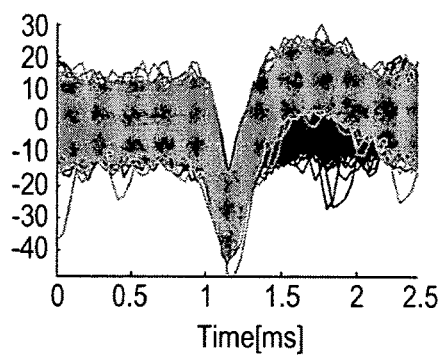
Figure 14K:
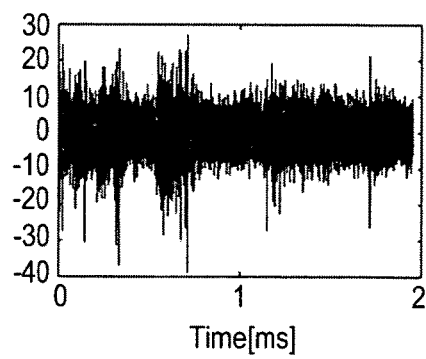
Figure 14L:
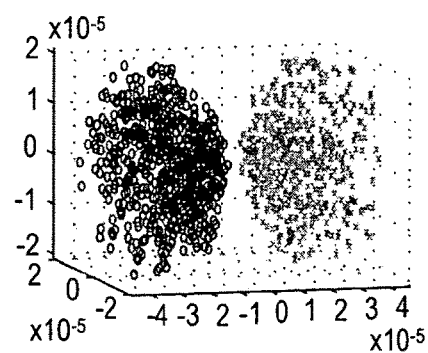

FIGS. 14A-14L show long-term neural electrophysiological recording capability in the brain. FIG. 14A shows percent of active chronically implanted MTEs able to detect at least 1 single unit (dashed line) as a function of weeks post-implant (n=7). FIG. 14B shows mean SNR of the largest single unit detected on each electrode. FIG. 14C shows mean amplitude of largest single unit detected on each electrode (solid, black), and the mean noise floor of each electrode (dashed, red). FIG. 14 has amplitude of single units from longest implant (solid, black). Amplitude of noise floor from same animal (dashed, red). FIGS. 14E-H show electrophysiological recordings taken from a rat with a MTE implanted in M1 five weeks post-implant. FIGS. 14I-L show electrophysiological recordings taken from a different rat implanted with a MTE in M1 seven weeks post-implant. FIGS. 14E and 14I shows mean waveform of discernable single units. FIGS. 14F and 14J show piled single units from two minutes of recordings. FIGS. 14G and 14K show representative example of two seconds of high-speed recordings. FIGS. 14H and 14L show results from principal component analysis showing distinct clusters.

DETAILED DESCRIPTION

Example embodiments are provided so that this disclosure is thorough, and will fully convey the scope to those who are skilled in the art. Numerous specific details are set forth such as examples of specific components, devices, and methods, to provide a thorough understanding of embodiments of the present disclosure. It is apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, component, region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Example embodiments will now be described more fully with reference to the accompanying drawings.

Implantable neural interface devices are important to a broad class of emerging neuroprosthetic and neurostimulation systems, in both research and clinical settings. In almost all cases, the performance of the system hinges to a large degree on the performance of the device to record and/or stimulate within quality, stability, and longevity requirements. Recording quality, longevity and stability is highly variable and the reactive tissue response that occurs to devices following implantation is a likely key contributing factor to diminishing the device performance. The fundamental challenge is to develop advanced materials and implantable structures that will enable neural interface devices to be implanted in vivo in target areas of an organism, such as in a brain, and remain functional for long durations, potentially for several years to several decades.

Penetrating neural probe technologies have allowed investigators to record both chemical and electrical signals in the brain. However, implantation of these neural probes causes acute tissue trauma with neuronal injury, recruitment of microglia, activation of astrocytes, and most importantly, disruption of the blood brain barrier (BBB) followed by plasma protein adsorption onto the surface of the probe. This acute trauma can cause abnormal electrophysiological responses, temporary increases in neurotransmitter levels, affect coating technologies, and perpetuate chronic immune responses.

While conventional carbon fiber microelectrodes can record single unit activity, patch clamp neural activity, and changes in extracellular dopamine concentrations, their ability to perform in vivo as a chronic recording device has been limited by the site size necessary to obtain single unit recordings and the insulation material, such as glass or fused silica, which has the negative effect of increasing the device's footprint and stiffness. Further computer models and experimental studies of the probe-tissue interface suggest that probes having greater flexibility may help to minimize perpetual mechanical trauma cause by physiological motion between the probe and surrounding tissue, as compared to trauma caused by conventional probe devices.

Recently, there has been an increased understanding of the detailed reactive tissue responses to implantable probes. Tissue encapsulation of the probe coupled with neuronal death in the vicinity of the recording electrode, have been implicated as the two largest variables negatively impacting the stability and longevity of long-term neural recordings. Regardless of the microelectrode technology used, cellular and acellular encapsulation forms around the electrode site. Tissue encapsulation has been implicated in an increase in electrode impedance, a decline in signal amplitude, increased noise, and possibly even the silencing of neurons. Many different approaches have failed to improve recording stability or mitigate the encapsulation around neural devices, including electrode surface modification, and stem cell delivery. Further, reduction of tissue encapsulation has also proven elusive for various conventional implantable, microscale sensors.

Developing smaller and more flexible neural probes with improved surface chemistry for long-term, high quality and selective neural recording is important for both neuroscience research and clinical neurotechnologies. Neural probes formed in accordance with the principles of the present disclosure, provide can provide monitoring of specific neuronal ensembles for long periods of time with great precision, which is a powerful tool in neuroscience research for linking low-level neuronal circuits to high-level brain function, such as learning, memory, and perception. On the clinical side, such a technology enables the development of closed-loop neurostimulation and neuroprosthetic systems using detailed neurophysiological signals for feedback. Beyond neural recording applications, long-lasting, high-fidelity neural interfaces directly benefit neurostimulation applications, as well.

Accordingly, this disclosure provides an innovative strategy that uses biocompatible polymers to develop new micro-components that in certain variations can be employed as electrodes in "microthread neural probes." Micro-components formed in accordance with the principles of the present disclosure provide excellent electrical and transduction properties. Such micro-component-based microthread neural probes are ultra-small (e.g., having sub-cellular dimensions) and flexible, with bioactive surfaces and nanostructured electrode sites for enhanced signal transduction.

In certain aspects, such micro-component electrode probes can be reliably inserted into a brain and used for chronic recording, having improved performance in chronic neural recording of spike activity, which is considered to be the most sensitive assay of neural interface material performance, for example. Design parameters of the micro-components include designing the size, flexibility, strength, conductivity, site electrical characteristics, insulating coating, insertion techniques, and electrode size.

Further, the inventive micro-components can be used in functionalized microthread neural probes for targeted intervention in chronic tissue responses. For example, immobilized biomolecules on a micro-component (e.g., microthread probe) surface can effectively interact with the surrounding environment to elicit, augment, or minimize specific reactive tissue responses, including biofouling, inflammation, and neurotoxicity.

The implantable device is sized according to the size of the patient's organ in which it is to be implanted. The present disclosure contemplates using micro-component devices independently implanted within target tissue or a target organ of a patient or alternately being used in conjunction with or coupled to medical devices or other types of medical implants, known to those of skill in the art, which are introduced and/or implanted internally in the patient. For example, to monitor the brain, the neural probe can be directly implanted through a burr hole in the skull of the patient. By way of another non-limiting example, such micro-electrodes can be used in cardiac pacemaker, monitoring assemblies, in/around peripheral nerves or a spine, under the skin, or in stents implanted in heart tissue or vasculature.

In various aspects, the inventive technology provides a micro-component that is relatively strong so that the micro-component is capable of being incorporated into a device that can be implanted in vivo and is relatively flexible to reduce potential stress at an interface with surrounding tissue to mitigate cellular damage adjacent to the micro-component. While not limiting the present teachings to any particular theory, flexible micro-components incorporated into implantable devices (e.g., neural probes) appear to advantageously produce less strain at a probe-tissue interface, and thus appear to advantageously reduce tissue response in chronic implantations. Micro-components incorporated into implantable devices, for example, as microelectrodes, can be used for electrophysiological recordings as well as recording the changes in concentration level of neural chemicals in the brain (such as dopamine) or in the body (such as NO, glucose, $pO_2$). In other embodiments, devices incorporating such micro-components, for example, as microelectrodes, may conduct electrical current or potential from an external source, for example, as a probe or in a cardiac pace-maker application. Devices incorporating such micro-components create long-lasting, high-fidelity neural interfaces, which may optionally further have biomimetic materials and surfaces. In certain variations, such micro-components are incorporated into advanced implantable neural probes for long-term (permanent), high quality and selective neural recording.

In various aspects, the micro-component is selected to have one or more dimensions that reduce damage in the surrounding tissue. As used herein, a "micro-component" has at least one spatial dimension that is less than about 100 µm (i.e., 100,000 nm), optionally less than about 50 µm (i.e., 50,000 nm), optionally less than about 10 µm (i.e., 10,000 nm), and in certain aspects less than or equal to about 5 µm (i.e., 5,000 nm). "Nano-sized" is generally understood by those of skill in the art to have at least one spatial dimension that is less than about 50 µm (i.e., 50,000 nm), optionally less than about 10 µm (i.e., 10,000 nm), optionally less than about 1 µm (i.e., less than about 1,000 nm).

In various aspects, the dimensions of micro-component are of a relatively small scale, for example, on a microscale. A "micro-component" as used herein encompasses "nano-components." It should be noted that so long as at least one dimension of the micro-component falls within the above-described micro-sized scale (for example, diameter), one or more other axes may well exceed the micro-size (for example, length). In certain variations, a micro-component of the present teachings can comprise a micro-fiber, which has an evident longitudinal axis or axial geometry, and further has at least one spatial dimension that is less than about 100 µm (i.e., 100,000 nm), optionally less than or equal to about 50 µm (i.e., 50,000 nm). In certain preferred variations, a microfiber component has at least one spatial dimension, such as a diameter, that is less than or equal to about 10 µm (i.e., 10,000 nm), optionally less than or equal to about 9 µm (i.e., 9,000 nm), optionally less than or equal to about 8 µm (i.e., 8,000 nm), optionally less than or equal to about 7 µm (i.e., 7,000 nm), optionally less than or equal to about 6 µm (i.e., 6,000 nm), and in certain aspects less than or equal to about 5 µm (i.e., 5,000 nm).

Thus, in certain aspects, depending upon the application, target location, and individual patient, a micro-component of the present teachings may have a major dimension, such as length, that is less than or equal to about 150 mm (15 cm), optionally less than or equal to about 100 mm (10 cm), optionally less than or equal to about 75 mm (7.5 cm), optionally less than or equal to about 50 mm (5 cm), optionally less than or equal to about 25 mm (2.5), optionally less than or equal to about 10 mm (1 cm), optionally less than or equal to about 5 mm, optionally less than or equal to about 1 mm, optionally less than or equal to about 0.9 mm (900 µm), optionally less than or equal to about 0.8 mm (800 µm), optionally less than or equal to about 0.7 mm (700 µm), optionally less than or equal to about 0.6 mm (600 µm), less than or equal to about 0.5 mm (500 µm), optionally less than or equal to about 0.1 mm (100 µm), optionally less than or equal to about 75 µm, optionally less than or equal to about 50 µm, optionally less than or equal to about 40 µm, optionally less than or equal to about 30 µm, optionally less than or equal to about 25 µm, optionally less than or equal to about 20 µm, optionally less than or equal to about 15 µm, and in certain aspects, optionally less than or equal to about 10 µm. In certain aspects, the micro-component has at least one major dimension (e.g., length) that is less than or equal to about 100 mm for implantation into a human patient's brain as a neural probe.

Stated in another way, in certain aspects, an ultra-small implantable device incorporates a single micro-component having a cross-sectional area of less than or equal to about 70 µm², optionally less than or equal to about 65 µm², optionally less than or equal to about 60 µm², optionally less than or equal to about 58 µm². In implantable devices comprising an array of such micro-components, a cross-sectional area of an ultra-small device can be less or equal to about 2,500 µm², optionally less than or equal to about 2,000 µm², optionally less than or equal to about 1,900 µm², optionally less than or equal to 1,800 µm², for example.

In various aspects, the inventive technology provides a micro-component that comprises a conductive core material. In accordance with the present teachings, the core material has a high electrically conductivity and therefore a low electrical resistivity, further is relatively strong for implantation, and is selected to be relatively flexible to reduce potential stress at an interface with surrounding tissue. In accordance with various aspects of the inventive technology, one or more discrete regions of a surface of the conductive core material are coated with an electrically conductive coating to form electrically conductive surface regions, which can facilitate charge transfer from the core material to an external conductor, such as an external electrode or other external lead. Such conductive regions provide nanostructured electrode sites for enhanced signal transduction in the micro-component.

The remaining regions of the surface of the core material, where the electrically conductive coating is absent, are coated in accordance with the present teachings with an electrically non-conductive (i.e., electrically insulating) biocompatible coating to render these surface regions electrically insulated and non-conductive. In certain variations, such an electrically non-conductive biocompatible material coating comprises a polymeric material that conforms to the surface of the core material to be insulated. In various aspects, the micro-component therefore comprises an electrically conductive core material having a surface with one or more discrete electrically conductive regions, where the remainder of the exposed surface of the core material has an electrically insulative coating. Such a micro-component can be employed as a micro-electrode for implantation as a medical device. While not limiting the inventive technology, in particularly preferred embodiments the micro-component microelectrode is used as a neural probe implanted in vivo into an organism's brain.

In certain aspects, the conductive core material is optionally selected to have a fiber shape. By "fiber" it is meant that the component defines an evident longitudinal axis and thus has a so-called "axial geometry." Fibers having such an evident longitudinal axis include an elongated axial dimension, which is longer than the other dimensions (e.g., diameter or width) of the fiber. In certain aspects, such elongated fiber components having an axial geometry have an aspect ratio (AR) defined as a length of the longest axis divided by diameter of the component, which is preferably at least about 100 and in certain aspects greater than about 1,000. In yet other aspects, such fibers may have an aspect ratio of 10,000 or more.

In various aspects, the core material has sufficient strength to penetrate into and through tissue, for example, brain tissue, without tearing and with minimal buckling. In various aspects, it is preferred that the electrically conductive core material comprises carbon. In certain aspects, such an electrically conductive core may comprise graphene. In certain embodiments, the core material comprises carbon nanotubes (CNTs), which are one-dimensional graphite sheets rolled up in the shape of seamless, hollow cylinders. Single-walled carbon nanotubes (SWNT) are formed from a single sheet of graphite, while multi-walled carbon nanotubes (MWNT) consist of multiple cylinders arranged in a concentric fashion. The typical diameters of SWNT can range from about 0.8 nm to about 2 nm, while MWNT can have diameters in excess of 100 nm. CNTs are known for their exceptional electrical conductivity, as well as mechanical properties. Metallic CNTs (e.g., CNTs exhibiting metallic behavior) can carry electrical current density more than 1,000 times greater than metals such Au, Pt or Ir. Furthermore, CNTs have exceptional tensile strength of $\sigma=200$ GPa and Young's modulus of $Y \approx 1.2$ TPa as well as flexibility and robustness, large surface area, chemical inertness and biocompatibility.

Carbon nanotube (CNT) films are strong, flexible, and conductive, with a sufficient design space that support creation of ultrathin and flexible microthread probes. The intrinsic properties of nanomaterials, such as nanocomposite CNT films, enable engineering the nano/micro organization of the probe to meet physical, chemical and biological requirements.

Transferring the unique mechanical and electrical properties of individual nanoscale CNTs to macroscale composite polymer structures is a challenging area in CNT technology. CNT composites traditionally prepared by polymerization and extrusion techniques have suffered from shortcomings such as phase segregation especially at high CNT concentration. The inability to load large amount of CNT into the composites have thus limited the ability to transfer the properties of nanotubes to the matrix.

In accordance with the present teachings, a deposition technique can be used called layer-by-layer assembly (LBL) provides a reliable method for fabricating CNT-polymer composites with favorable characteristics. The principle of the LBL technique relies on alternating adsorption of polyelectrolytes onto a substrate. The layers are built up by sequential dipping of the substrate into oppositely charged polyelectrolyte solutions (FIG. 9, upper portion). Monolayers of individual components attracted to each other by electrostatic and van-der-Waals interactions are sequentially adsorbed on the substrate.

Single-walled carbon nanotubes (SWNTs) are well suited for microthread neural probes because of their unique mechanical, and electrical, properties. LBL films can be constructed on a variety of solid substrate, thus imparting much flexibility for size, geometry and shape and further patterned or etched (with chemicals, plasma, electron beam, or high intensity lasers, for example). Following film fabrication by the LBL process, the film can be detached from the substrate to yield free-standing, flexible and conductive samples. The electrical conductivity of the LBL films of SWNTs even in non-optimized conditions is $1.5*10^3$ S/cm, with ultimate conductivity of individual SWNTs of $1*10^4$ S/cm. This is at least one order of magnitude greater than the conductivity of the conducting polymer PEDOT, and equal or better than the conductivity of sputtered multicrystalline $IrO_x$, which is one order less than that of the single crystals.

Additionally, LBL multilayers have both ionic and electronic conductivity that provides favorable charge transfer characteristics. The tubular morphology of the films is similar to that of PEDOT tubes that show drastic increase of charge storage capacity and equally drastic decrease of impedance.

In certain aspects, the tensile strength of SWNT LBL films is $\sigma$>430 MPa, which is substantially greater than that of polyimide films conventionally used as a backing for advanced implantable electrodes (PYRALIN, $\sigma$=350 MPa). Lateral orientation of nanotubes of LBL assemblies greatly enhances their mechanical properties as opposed to the nanotube "forests" when CNTs are grown from the surface. Nanotubes attached to the substrate only by the end can be easily broken off. This can occur as a result of tissue micromotion, as well as during the implantation procedure. A CNT film formed in accordance with these techniques is exceedingly flexible in all directions, with excellent tensile strength. The thin polymer electrically non-conductive coating, discussed in more detail below, is also flexible. When the microcomponent comprises a core material of CNT film, it can form a complete microthread that is (qualitatively) significantly more flexible than the best performing microfabricated thin-film polymer probes currently available, which are typically 12-15 µm thick.

In certain embodiments, the core material comprises a carbon fiber, which has good flexibility, high electrical conductivity, and can be made with a 5 to 10 µm diameter. As noted above, in various aspects, the core material has sufficient strength to penetrate into and through tissue, for example, brain tissue, without tearing and with minimal buckling. In this regard, carbon fibers are particularly advantageous, since a typical 2 mm long intracortical implant carbon fiber has a nominal value of stiffness (k)=(cross-sectional area×elastic modulus)/length, 4,500 N/m and a nominal value of spring constant $(k_c)$=$3\pi$(elastic modulus) [(outer diameter)$^4$−(inner diameter)$^4$]/(64×length$^3$) of about 0.01 N/m.

Certain desirable carbon fibers can have an elastic tensile modulus of greater than or equal to about 200 GPa, for example between 240 GPa to about 999 GPa and can exhibit a modulus of elasticity up to 531 GPa, shear modulus of 2.2 GPa, and a tensile strength up to 5.65 GPa. Comparatively, the elastic modulus for typical carbon fibers (e.g., 234 GPa) is far greater than that of silicon (164 GPa). Such physical properties make carbon fibers a desirable choice as a core material for the micro-component electrodes in accordance with certain aspects of the present teachings. In other alternate variations, the conductive core may comprise gold (which has a tensile modulus of 78.5 GPa), platinum, tungsten, steel, iridium, or a conductive composite material formed by layer-by-layer assembly techniques. Thus, in certain aspects, the electrically conductive core comprises a metal selected from the group consisting of gold, platinum, tungsten, steel, iridium, or combinations thereof.

While not limiting the present disclosure to any particular theory, it is theorized that neural probes with a dimension under about ten, and more desirably under about seven, micrometers reduce the foreign body response of an organism by preventing cellular adhesion or spreading. Therefore, in certain variations, the conductive core material comprises a carbon fiber having a cross-sectional diameter of less than or equal to about 12 µm, optionally less than or equal to about 10 µm, optionally less than or equal to about 9 µm, optionally less than or equal to about 8 µm, in certain preferred aspects, optionally less than or equal to about 7 µm, optionally less than or equal to about 6 µm, and in certain variations, optionally less than or equal to about 5 µm.

The core material (e.g., CNT strand) is the electrically conductive part of the probe when it is incorporated into such a device as shown in FIGS. 8 and 12, with an exposed tip comprising the electrically conductive region(s) or electrode site. A conformal insulative (non-conductive) polymer coating provides electrical insulation along the length of the core material, as well as a substrate for functionalization by attaching biomolecules. In certain embodiments, the cross-sectional dimension of a CNT strand is approximately 5×5 µm or 1 µm×5 µm, which when combined with the approximately 0.5 to 1 µm insulator coating has desired sub-cellular size dimensions (thinnest assembled strand is about 2 µm).

In various aspects, the insulative electrically non-conductive material is a polymer coating or optionally can also be a resistive layer-by-layer coating, used both as dielectric coating with high impedance and as reactive base layer for further surface modification. Reactive parylene coatings are particularly suitable, because they are conformal, thin, and therefore relatively flexible. Further, reactive parylene coatings combine the well-established high resistivity of conventional parylene with the ability to provide chemical anchor groups for subsequent modification with hydrogels or immobilization of biomolecules.

In various aspects, the insulative non-conductive material coating is biocompatible. In various embodiments, biocompatible polymers are used on a conductive carbon containing core, such as a carbon fiber, to make ultra-small neural probes that are flexible, yet durable, robust, and that desirably have advanced bioactive capabilities for controlling intrinsic biological processes. In certain embodiments, the insulative material coating disposed on and forming the non-conductive regions of the core material's surface has a thickness of less than or equal to about 1 µm, optionally less than or equal to about 950 nm, optionally less than or equal to about 900 nm, optionally less than or equal to about 850 nm, optionally less than or equal to about 800 nm.

The insulator coatings can be optionally functionalized. In various embodiments, suitable insulator coatings can be vapor-deposited and/or micro-patterned functional polymer coatings. In certain embodiments, suitable insulator coatings are based on a novel class of vapor-deposited polymers referred to as functionalized poly-p-xylylenes (FIGS. 10 and 11). These polymer coatings are similar to the commercially used parylene coatings in that they can be deposited conformally on a wide range of different substrates, but, in addition, provide versatile anchor groups for sophisticated surface modifications with a wide range of different surface chemistries. Hence, this technology enables a one-step coating procedure to generate functionalized surfaces without requiring any kind of post-treatment once the films are deposited. The resulting polymers provide chemically reactive anchor groups for further surface modifications. Reactive coatings are compatible with soft lithographic processes, allowing for patterning of DNA, proteins, sugars, and mammalian cells, by way of non-limiting examples. In addition to the widespread availability of "anchor groups," the simplicity in providing a wide range of functional groups, the excellent adhesion to various substrata, and its applicability to surfaces with three-dimensional geometries are key advantages when compared to polymers deposited by solvent-based methods. Further, such a technology has been successfully employed to develop protein resistant coatings.

Leading-edge reactive coatings can support regioselective immobilization of bioligands via Husigen heterocycloaddition (so-called "click chemistry"), or can result in highly non-fouling, protein- and cell-resistant surfaces. The latter is achieved by functional CVD-coatings that can initiate atom-transfer radical polymerization (ATRP), followed by surface-induced graft-polymerization to create well-defined hydrogel films. The use of CVD-based initiator coatings provides access to synthetic polymer hydrogels based on acrylates and methacrylates, which have gained widespread popularity in various biomedical applications such as drug-delivery and tissue engineering.

Thus, in one embodiment, the insulative non-conductive coating comprises a parylene-N insulator layer coated via chemical vapor deposition (CVD) on the surface of the core material, for example at an exemplary thickness of about 800 nm. In certain embodiments, the basic configuration of a single-strand microthread probe is a thin, flexible and conductive CNT strand that is coated with a thin, conformal insulative layer of functionalized poly-p-xylylenes (PPX—a biocompatible coating material closely related to parylene) along its length, except for its tip (FIG. 8A). The core material (e.g., CNT strand) is the conductive part of the probe, with an exposed tip comprising the electrically conductive region or electrode site. The conformal insulative polymer coating provides electrical insulation along the length, as well as a substrate for functionalization by attaching biomolecules.

By way of non-limiting example, one insulative coating comprises parylene-N and can be formed by one gram (1 g) of paracyclophane being sublimed at 90-110° C. and 0.3 mbar and carried into the pyrolysis chamber by argon at a flow rate of 20 sccm. After pyrolysis at 670° C., the polymer is deposited on the substrate at 15° C. The deposition rate, according to the QCM, is 0.6-1.0 Å/s.

In certain aspects, the insulative non-conductive material coating is treated or comprises one or more biofunctional agents. By way of further background, neuronal loss and glial encapsulation surrounding neural prostheses are well documented phenomena, although the mechanisms underlying these changes in the device-tissue interface remain largely unexplored. Inflammation in the organism plays a role; the release of inflammatory cytokines from cells attached to explanted probes has been demonstrated, and anti-inflammatory drugs such as dexamethasone have reduced astrogliosis associated with probes in vivo. Kim et al. report evidence of reduced in vivo impedance associated with dexamethasone-releasing probes implanted in guinea pigs for a three week time course (Kim and Martin 2006).

In recent years, a contribution of cell-cycle re-entry to the activation of glia, as well as neuronal apoptosis, has been demonstrated in models of central nervous system (CNS) injury. The cell cycle is a complex process through which cells progress from a quiescent to a proliferative state, and cellular advancement through this cycle is controlled by cyclin dependent kinases (CDKs) and associated cyclins. Following CNS injury and an associated upregulation of these cell-cycle proteins, mitotic cells (namely, microglia and astrocytes) proliferate, while non-mitotic cells (differentiated neurons) undergo caspase-mediated apoptosis. Flavopiridol is a flavonoid drug which is a broad CDK inhibitor and arrests progression through the cell cycle. Di Giovanni et al. showed a single injection of flavopiridol intracerebroventricularly reduced expression of the cell cycle protein cyclin D1, decreased neuronal cell death, reduced glial activation, and improved motor and cognitive recovery following traumatic brain injury in rats. Flavopiridol has resulted in improved functional and histological outcomes in vitro and in vivo models of spinal cord injury, Parkinson's disease, motor neuron apoptosis, and excitotoxic injury.

Since brain injury involves multiple biochemical pathways (i.e., oxidative stress, excitotoxicity, and inflammation) and complex signaling cascades, treatment strategies that target multiple mechanisms appear to be an optimal solution. In other medical pathologies, such as cancer and AIDS, the effect of multiple therapeutic agents has proven to be greater than that of the sum of the single counterparts. Advantageously, the micro-component electrodes for implantable neural medical devices prepared in accordance with the present disclosure have the ability to present multiple biofunctional or therapeutic agents to the surrounding environment and tissue (e.g., combinational drug therapy), which is believed to provide benefits for therapy for traumatic brain injury. By way of non-limiting example, flavopiridol and minocycline have been observed to have synergistic effects in preserving hippocampal neurons following ischemic brain injury in rats. Alternative dosing regimens are an additional opportunity for optimizing effects on recording stability and quality.

In various aspects, the micro-component electrodes of the present disclosure provide one or more of the following attributes that are desirable for enhanced long-term tissue interface with an implanted medical device: (1) Minimizing biofouling—the adsorption of non-specific proteins to probe surfaces—including for example, blood-borne proteins resulting from disruption of the blood-brain barrier during probe insertion—which can provide inflammatory signals and degrade electrical characteristics; (2) Minimizing immune responses involving cellular responses (primarily astrocytes and microglia) that tend to encapsulate probes over time; and (3) Minimizing neurotoxic processes involving both direct neuron damage, as well as deleterious extracellular signaling, oxidative stress, and the like.

Therefore, in certain embodiments, immobilized biomolecules on the exposed microcomponent surfaces can be effective for intervening with specific reactive tissue responses, including biofouling, inflammation, and neurotoxicity. It is believed that micro-component surfaces that do not become bio-fouled (i.e., have little non-specific protein adsorption) elicit subsequent attenuated reactive tissue responses and improved electrical characteristics. Therefore, in certain embodiments, the electrically non-conductive biocompatible material coating is treated or comprises one or more agents that i) reduce the accumulation and/or attachment of microorganisms or cells to the surface of the insulative coating, therefore serving to minimize or reduce bio-fouling or other undesirable cellular growth and/or ii) otherwise interact with the surrounding environment in a predetermined way. "Biofilm resistant" or "biofouling resistant" refers to any coating or agent that impairs, inhibits, prevents or retards the attachment and/or growth of biofouling organisms or cells.

In certain aspects, the insulative electrically non-conductive coating may comprise one or more "biofunctional" or "bioactive" substances, which refers to a chemical substance, such as a small molecule, active ingredient, macromolecule, metal ion, or the like, that causes an observable change in the structure, function, optical function, or composition of a cell when a cell is exposed to such a substance. In various aspects, the biofunctional substance or agent promotes cell regeneration, differentiation, growth, proliferation, and/or repair, for example.

Functional bio-coatings and anti-biofouling coatings, such as poly(ethylene glycol) (PEG), are beneficial for their ability to improve chronic neural interfaces. Therefore, in certain variations, the present disclosure provides methods of making a micro-component electrode that comprises coating an electrically conductive core material with a non-conductive material. The non-conductive material can further be functionalized. For example, in one embodiment, the micro-component core material surface is coated with an 800 nm layer of parylene-N via chemical vapor deposition and then modified by using a functionalized parylene with poly(ethylene glycol) (PEG) poly(ethylene glycol)-terminal methacrylate (PEGMA) as a biofunctional substance. Poly (ethylene glycol) methacrylate can be immobilized onto the parylene surface by several different methods, including but not limited to atom transfer radical polymerization and grafting to a functionalized coating.

By way of example, poly[(p-xylylene-4-methyl-2-bromoisobutyrate)-co-(p-xylylene)] is optionally used as initiator for atom transfer radical polymerization (ATRP) because of its functional groups. After chemical vapor deposition of poly[(p-xylylene-4-methyl-2-bromoisobutyrate)-co-(p-xylylene)], the micro-component electrodes are incubated under inert conditions with degassed aqueous solution of oligo(ethylene glycol) methyl ether methacrylate, with CuBr/CuBr2/bpy as the catalyst. The polymerizations proceed at room temperature for 4 hours. Microthread electrodes are thoroughly rinsed after the reaction.

In one exemplary method used to create the initiator coatings for ATRP via CVD polymerization, poly(p-xylylene-4-methyl-2-bromoisobutyrate-co-p-xylylene) (2) in FIG. 10 is prepared via CVD polymerization in a custom-made CVD polymerization system. The starting material, [2.2]paracyclophane-4-methyl 2-bromoisobutyrate (1), is sublimed under vacuum and converts by pyrolysis into the corresponding quinodimethanes, which spontaneously polymerizes upon condensation to the cooled substrate surface, which is maintained at 15° C. Throughout CVD polymerization, a constant argon flow of 20 sccm and a working pressure of 0.5 mbar are maintained. The pyrolysis temperature is set to be 550° C. and sublimation temperatures are between 115-125° C. under these conditions. CVD polymerization spontaneously occurs on samples placed on a rotating, cooled sample holder. In cases, where patterned substrates are required, polydimethylsiloxane (PDMS) micro-stencils can be sealed to the substrates during CVD polymerization. Next, an aqueous solution of the methacrylate, 2,2'-bipyridine (bpy), and $CuBr_2$ is stirred in a Schlenk flask at room temperature. The homogeneous solution can be degassed using three freeze-pump-thaw cycles. Next, copper bromide is added under nitrogen purge to the frozen solution and the molar ratio of $CuBr/CuBr_2/bpy$ can be set to be 1/0.3/2.5. The mixture is warmed up to room temperature and stirred until a homogeneous dark brown solution is formed. The solution is then transferred into a nitrogen-purged glovebag, and the polymerizations proceed at room temperature for a set reaction time. Samples are analyzed in triplicate. To prepare samples for protein adsorption and cell adhesion studies, the CuBr concentration is 10 mM and polymerizations is allowed to proceed for three hours at room temperature.

The use of CVD-based initiator coatings provides access to a variety of biofunctional materials, including synthetic polymer hydrogels based on polyethylene glycol methacrylates (PEGMA), which have protein resistant properties. Beyond PEGMA, certain methacrylate-based monomers with different side functional groups are contemplated, which impart protein-resistant properties to the coated surfaces. These monomers can be deposited after CVD polymerization via graft-co-polymerization (FIGS. 10 and 11) from ATRP initiator groups. In certain aspects, monomers are 2-hydroxyethyl methacrylate (HEMA), poly(ethylene glycol) methyl ether methacrylate (PEGMA), 3-sulfopropyl methacrylate potassium salt (SMPS), [2(methacryloyloxy) ethyl]dimethyl-(3-sulfopropyl) ammonium hydroxide (MEDSAH), and combinations thereof.

In certain variations, during ATRP polymerization, anti-inflammatory molecules, such as dexamethasone can be added to the polymerization solution and loaded into the hydrogel layer. In this way, a depot layer is created that can release dexamethasone during initial implant periods, thereby reducing the early onset of inflammatory responses. Alternatively, interlukin (IL-10) may be used as anti-inflammatory component. IL-10 is a small protein and is therefore structurally and functionally different from dexamethasone. Dexamethasone and IL-10 can be incorporated together during this process, as well. A variety of other biofunctional materials can be incorporated into the insulator coating in this manner.

In another exemplary method for grafting PEG to the parylene coating, poly(p-xylylene carboxylic acid pentafluorophenolester-co-p-xylylene) is selected because it is a polymer with an active ester group that can readily react with primary amine. After chemical vapor deposition of poly(p-xylylene carboxylic acid pentafluorophenolester-co-p-xylylene), micro-component electrodes are incubated in 10 mM mPEG-$NH_2$ (MW 10,000) PBS solution for 8 hours, followed by thorough rinses.

FIGS. 11A-11F shows an exemplary formation of a parylene coating that is further functionalized by ATRP applied to a conductive core material to form a micro-component of the present disclosure. Such a micro-component has a sub-cellular cross-sectional dimension, but is flexible, stronger, and with sufficient electrical characteristics for neural recording and advanced bioactive capabilities for controlling intrinsic biological processes. 7 μm diameter (tensile modulus 234 GPa) carbon fibers are first mounted onto a microelectrode printed circuit board. The carbon fiber is then coated with an 800 nm poly(p-xylylene) coating via chemical vapor deposition (CVD) polymerization (FIG. 11A). Poly(p-xylylene) (also know under the trade name Parylene-N™) is selected for its very low dissipation factor, high dielectric strength, and low dielectric constant that is also invariant with frequency.

One, two, or three individual 7 μm diameter (tensile modulus=234 GPa) carbon fibers are mounted onto a NeuroNexus A16 printed circuit board or a bare stainless steel wire using silver epoxy (WPI; Sarasota, Fla.) and baked at 140° C. for 10 min. An approximately 800 nm thick poly (p-xylylene) insulator layer is then coated via CVD. One gram of paracyclophane is sublimed at 90-110° C. and 0.3 mbar and carried into the pyrolysis chamber by argon at a flow rate of 20 standard cubic centimeters per minute (sccm). After pyrolysis at 670° C., the polymer is deposited on the substrate at 15° C. The deposition rate, according to the QCM is 0.6-1.0° A/s.

An additional 50 nm thick layer of the functionalized polymer coating poly[(p-xylylene-4-methyl-2-bromoisobutyrate)-co-(p-xylylene)] is deposited onto the device via CVD polymerization (FIG. 11B). This polymer provides initiator groups for subsequent atom transfer radical polymerization (ATRP). After ATRP, a poly(ethylene glycol methacrylate) (PEGMA) top layer is formed that is about 200 nm thick (FIG. 11C), which renders the neuronal probe devices protein-resistant.

Poly(ethylene glycol methacrylate) is grafted onto the poly(p-xylylene) surface by atom transfer radical polymerization (ATRP). Poly[(p-xylylene-4-methyl-2-bromoisobutyrate)-co-(p-xylylene)] is used as initiator for ATRP because of its functional groups. After CVD polymerization of poly[(p-xylylene-4-methyl-2-bromoisobutyrate)-co-(p-xylylene)], MTEs are incubated under inert conditions with a degassed aqueous solution of oligo(ethylene glycol) methyl ether methacrylate, with CuBr/CuBr2/bpy as the catalyst. The polymerizations proceed at room temperature for 4 hours. MTEs are thoroughly rinsed after the reaction.

In certain aspects, the methods of making a micro-component electrode further comprises coating the electrically conductive core material with an electrically conductive material, to form a recording site, for example. Such a process may be preceded by cutting a portion of the conductive core material having the applied non-conductive coating and then applying the electrically conductive material to the exposed region. For example, a recording site is created by electrochemical deposition of poly(3,4-ethylenedioxythiophene) poly(styrenesulfonate) (PEDOT/PSS) onto the tip of the neuronal probe, from which the poly(p-xylylene) and poly(ethyleneglycol) methacrylate coatings are removed (FIG. 11D). Poly(p-xylylene)-coated and PEGMA-grafted carbon fibers are cut to a length of 0.3-0.5 cm. For PEDOT deposition, monomer 3,4-ethylenedioxythiophene (EDOT) (Bayer, Germany) is electrochemically polymerized and deposited onto the surface of the electrode sites together with the anions in the solution. Specifically, PEDOT/PSS is electropolymerized from a 0.1 M poly (sodium-p-styrenesulfonate) (PSS) (Acros Organics; Morris Plains, N.J.) aqueous solution with an EDOT concentration of 0.01 M under galvanostatic conditions. In galvanostatic mode, the current is held at 100 pA. FIG. 11D shows removal of insulation by cutting away the tip to expose a carbon site, which is then electrodeposited with PEDOT.

The combination of such advanced materials provides an ultra-small organic interface that has the approximate size of a single trace of a conventional silicon neural probe, but advantageously has sufficient strength and flexibility to act as a stand-alone independent electrode.

FIGS. 12A-12D show exemplary schematics and cross section of architecture of a neural probe incorporating a micro-component electrode in accordance with one aspect of the present teachings. FIG. 12A shows a first side view of an exemplary neural probe on a printed circuit board (10-8 mm) and FIG. 12C shows a second exemplary neural probe on a printed circuit board (5-3 mm) made in a manner similar to that described above in the context of FIGS. 11A-11F. In the sectional view (FIG. 12C of the probe in FIG. 12A), a conductive core comprises carbon, which is coated with a parylene coating, followed by a PPX-PEG coating. FIG. 12D shows a detailed sectional view of the layers forming an exemplary MTE probe, where the conductive core comprises carbon, which is coated with a parylene coating, followed by a PPX-PEG coating. At a terminal end, the probe is cut and PEDOT is applied.

In certain aspects, the CVD technology provides bioconjugation of active biomolecules to the micro-component electrode surface. While the bioconjugation chemistry can be easily adapted by changing the coupling groups incorporated in the CVD polymer, an exemplary group discussed herein is neural cell adhesion molecule (NCAM). NCAM can exhibit neuroprotective as well as neurotrophic properties. Another exemplary coupling group for immobilization along the insulator coating surface is the growth brain-derived neurotrophic factor (BDNF) growth factor, used independently or in conjunction with NCAM. Notably, various proteins, ligands, saccharides, and other bioactive molecules can be selected and used in various combinations for immobilization of proteins onto CVD films. In certain aspects, the orientation of biofunctional substances (requiring specific active regions to be exposed to the surrounding environment) on the surface of the insulator coating can be achieved by a variety of methods. Such techniques include using a reaction of BDNF with Msc-ONSu, so that protective groups are successively introduced in a protein yielding pure fractions isolated by ion exchange chromatography. Glycosaminoglycans, such as heparin, are also immobilized onto CVD coatings. Simultaneous immobilization of two different proteins, here NCAM and BDNF, in controlled ratios using bio-orthogonal immobilization strategies are contemplated. Quantification of surface-bound biomolecules is done by surface plasmon resonance spectroscopy (Biacore X) on CVD-coated gold slides.

In various aspects, the micro-components have one or more conductive regions formed on the surface of the conductive core material, to serve as nanostructured electrode sites for enhanced signal transduction to the core material from an external electrical source. Such electrically conductive electrode sites optionally have geometric surface areas ranging from about 100 $\mu m^2$ to 500 $\mu m^2$ (corresponding to an uninsulated tip about 5 to 25 microns long assuming all sides are not coated), which is consistent with sizes of conventional microelectrodes for unit recording.

In yet other aspects, at least one of the electrically conductive core material or the electrically non-conductive biocompatible coating of the implantable micro-component electrode are optionally patterned, shaped, and/or etched. Thus, the electrically conductive core material or the electrically non-conductive biocompatible coating of the implantable micro-component electrode can be treated prior to implantation. Such patterning, shaping, and/or etching can be achieved by techniques that employ wax or resists, photolithography, electron beam, laser, and/or plasma treatment, by way of non-limiting example.

In certain embodiments, one or more of the electrically conductive regions may be formed by removal of the insulative electrically non-conductive coating after application, for example, by mechanical removal (e.g., cutting and/or scraping) or by ablation (e.g., laser ablation). In other embodiments, one or more of such regions may be formed by masking the desired areas along the surface of the core material prior to application of the electrically non-conductive insulative coating. Using a wax coating for example, the tip of a carbon fiber can be shielded from parylene coating during the CVD process. Then, after applying the parylene electrically non-conductive coating over the wax, the wax can be melted away in hot ethanol. In other aspects, such regions may be formed by removing the insulative coating and then applying the electrically conductive material to the regions. By way of non-limiting example, a carbon electrode site (approximately 38.5 µm$^2$) is exposed by cutting a discrete region of the surface of the insulator-coated (parylene-coated) carbon core material to create the region to be coated with a conductive material.

One particularly suitable electrically conductive material is a biocompatible conductive polymer, poly(3,4-ethylene dioxythiophene) (PEDOT) with a poly(4-styrenesulfonate) (PSS) counter-ions. Such a PEDOT:PSS conductive polymer is electrochemically deposited onto the exposed carbon core material to decrease recording site impedance. For PEDOT deposition, monomer 3,4-ethylenedioxythiophene (PEDOT) (Bayer) is electrochemically polymerized and deposited onto the surface of the electrode sites together with the anions in the solution. Specifically, PEDOT/PSS is electropolymerized from a 0.1 M poly(sodium-p-styrenesulfonate) (PSS) (Acros Organics; Morris Plains, N.J.) aqueous solution with a PEDOT concentration of 0.01 M under either galvanostatic conditions. In galvanostatic mode, the current is varied from 50 to 500 pA. Presence of PEDOT/PSS is confirmed with cyclic voltammetry and electrochemical impedance spectroscopy. Other suitable conductive biocompatible materials for coating the one or more conductive regions on the surface of the core material include polypyrrole, platinum, platinum black, iridium oxide, carbon nanotubes, graphene, and combinations thereof.

In various aspects, an impedance of a core material comprising carbon is typically about 2.5 MΩ to about 6 MΩ. Thus, in various embodiments, the conductive materials for the one or more conductive regions on the surface are selected to reduce the impedance of the core material surface at the interface electrically communicating with an external electrical lead. For example, conductive coatings comprising PEDOT can have an impedance of less than or equal to about 500 kΩ to greater than or equal to about 10 kΩ. In certain aspects, the PEDOT may have an impedance ranging from about 10 to about 500 kΩ; and in certain aspects, may range from greater than or equal to about 100 kΩ to less than or equal to about 500 kΩ. Other suitable materials include platinum black (PtB), which typically has an impedance of greater than or equal to about 800 kΩ to less than or equal to about 2.5 MΩ.

In certain aspects, the present disclosure incorporates the micro-components into a single-strand microthread probe (having the electrically conductive region/site at the tip) and 1-dimensional linear electrode arrays (array of conductive sites positioned along the axial dimension). In certain embodiments, the multi-strand probes optionally have multiple conductive region sites (for example, up to 8 sites, with 30 to 200 µm site separations). These types of base assemblies can be modified to more complex two- and three-dimensional microthread probe arrays, as well.

In certain variations the present teachings contemplate the incorporation of the micro-components into assemblies that form microthread arrays for long-term and high fidelity in vivo (e.g., neural interfaces). While not limiting the present disclosure in any particular manner, microelectrode probes of the present teachings are capable of the following: (1) recording useful spike activity from cortex and deeper structures for a duration of more than six months; (2) a superior recording quality; (3) increased stability and diminished degradation of in vivo recordings. Therefore, in certain variations the micro-component electrodes of the present disclosure increase the quality, stability, and longevity of neural recordings.

In certain embodiments, microthread electrodes (MTEs) comprising micro-components are prepared by mounting individual 7 µm diameter (tensile modulus 234 GPa) carbon fibers onto an acute microelectrode printed circuit board. (FIG. 8). The device is then coated with 800 nm parylene-N coating via chemical vapor deposition CVD. A carbon electrode site (approximately 38.5 µm$^2$) is exposed by cutting the parylene coated carbon. See for example FIGS. 1A-C. Contact pins are gently scraped using a scalpel, and a carbon electrode site is exposed by cutting the parylene coated carbon fiber with a pair of scissors. Poly(3,4-ethylene dioxythiophene) (PEDOT) with a poly(4-styrenesulfonate) (PSS) counter-ion is electrochemically deposited onto the exposed carbon to provide an electrically conductive region on the surface of the carbon core that serves as a recording site and to decrease recording site impedance (FIGS. 1C-E). Such a neural implant has ultra-small dimensions (e.g., 38.5 µm$^2$ electrode size and 58 µm$^2$ footprint), while also demonstrating flexible, robustness, and durability.

Figure 2E:
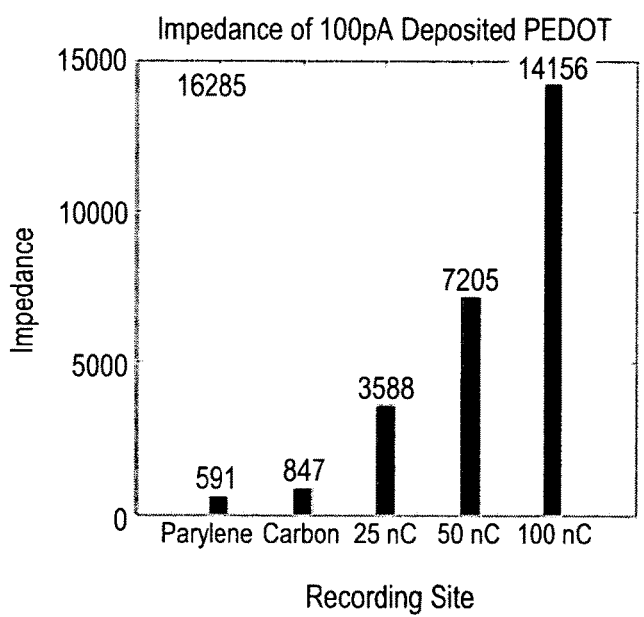

Cyclic voltammetry (CV) measurements are made on parylene coated carbon fibers, parylene coated fibers with a approximately 38.5 µm$^2$ exposed carbon tip, and a parylene coated fiber with an exposed PEDOT/PSS recording site (FIG. 2A). CV profiles indicate the presence of PEDOT on the recording site. Impedance spectroscopy (EIS) measurements displayed progressive decrease in impedance (FIGS. 2B-2D) with increased PEDOT deposition. Also as expected, charge storage capacity increased with longer PEDOT deposition durations (FIG. 2E).

The microthread probes are manually inserted into rat cerebral cortex to validate the insertion technique. In vivo cortical recordings with PEDOT deposited, parylene insulated carbon fibers are able to record neural spikes in rat motor cortex. (FIGS. 3A-B). In all in vivo trials, the PEDOT coated MTE is able to detect at least one neuronal spike with a signal to peak-to-peak-noise ratio (SNR) of greater than 1.1 ranging up to 8.0. In contrast, comparative parylene insulated carbon fibers with a cut carbon exposed recording site are unable to record any neuronal spikes with an SNR greater than 1.1. The PEDOT deposited MTEs is able to record local field potential (LFP) activity. A comparative uninsulated carbon fiber lacking the conductive PEDOT coating implanted 2 mm into the cortex is able to record LFPs, but unable to discriminate any single unit spikes—indicating the necessity of insulating the fiber to provide a more localized recording environment.

Thus, comparative parylene insulated carbon fibers with a cut carbon exposed recording site (without a conductive coating) is unable to record any neuronal spike with an SNR greater than 1.1. Interestingly, the PEDOT MTE prepared in accordance with the present disclosure had higher peak to peak noise then the carbon site MTE (FIGS. 3C-3E). The increased noise floor may be due to biological noise. The PEDOT MTE is able to pick up neuronal spikes from many distant neurons to increase the noise floor. By using a carbon site MTE reference for example, more neurons can be discriminated from the background.

Spectrograms show more detailed low-frequency activity as a function of time during a typical recording segment (FIGS. 4A-C). Settings for the spectrogram are the same as with the power spectral densities, except sliding 1-second windows are used to observe changes throughout a short recording session. Recordings from the PEDOT fiber depict oscillatory activity around 4-Hz in the theta band that occurs in burst throughout the recording session (FIG. 4A); this is typically referred to as a ketamine spindle bursting activity. Recordings from the bare carbon site are dominated by a 60-Hz instrumentation noise throughout the session, which is not observed from the PEDOT fiber. However, low frequency theta-band activity is sufficiently large in amplitude to be observed from the carbon electrode, even though individual neural spike activity is not present during the recording sessions.

In summary, novel microelectrodes are provided with reduced feature size that is able to record single unit spikes. This is the smallest neuronal recording electrode site that PEDOT has been grown onto. It is also the smallest implanted probe to successfully record single unit activity in the cortex. The stiffness (k) of an exemplary MTE prepared in accordance with the present teachings is calculated from the cross sectional area, elastic modulus and length and 2 mm length is 4,500 N/m which is an order of magnitude smaller than a commercially available silicon microelectrode of the same length, 151,000-246,000 N/m. The spring constant ($k_c$) of an exemplary MTE is calculated to be 0.01 N/m while a commercially available silicon microelectrode of the same length is 2.13-3.46 N/m in the planar dimension and 149-615 N/m in the lateral dimension.

FIG. 4A depicts the power spectral densities of the neural recordings showing the intensity of the recordings as a function of frequency. These are created using a Hamming window for smoothing with a 32768-point FFT. Low frequency activity in the range typically observed for local field potentials is presented. The peak at 0-Hz is indicative of a slight DC-offset in the signal in the recordings. Peaks observed at 4-Hz and 10-Hz are representative of low-frequency synchronous activity in the theta and alpha bands respectively. Pronounced theta-band activity is typically observed under ketamine anesthesia, which is used here.

In certain alternate embodiments, the one or more conductive regions on the core material (e.g., the recoding sites) are made from other high impedance materials such as gold (gold can be further modified—for example by using self-assembled monolayers). A wax is placed onto a silicon wafer and spun to a certain thickness. The length of the exposed carbon site can be controlled by controlling the thickness of the wax on the wafer, where faster spins leads to a thinner wax layer. CVD of parylene is carried out. Then, the parylene over the wax and the wax can be melted away in hot ethanol. In such embodiments, the micro-component can be used as an electrode for chemical sensing, such as dopamine.

In certain aspects, the present disclosure provides methods of monitoring, sensing, or stimulating neural activity in an organism. In one aspect, such a method comprises electrically communicating with a probe implanted into an organism. In certain variations, the method comprises electrically communicating with a neural probe implanted into a brain of an organism. The probe optionally has a cross-sectional area of less than or equal to about 2,000 micrometers-squared ($\mu m^2$) and comprises at least one micro-component electrode. The at least one micro-component electrode comprises an electrically conductive core material having a surface with one or more electrically conductive regions disposed on the surface of the electrically conductive core material. The one or more electrically conductive regions disposed on the surface of the electrically conductive core comprise an electrically conductive polymeric coating. Further, an electrically non-conductive polymeric coating is disposed on regions of the surface of the electrically conductive core material corresponding to locations where the one or more electrically conductive regions are absent. In certain preferred variations, the micro-component electrode has at least one dimension less than or equal to about 10 μm.

In certain variations of the present technology, a neural probe is able to detect at least one neuronal spike with a signal to peak-to-peak noise ratio (SNR) of greater than or equal to about 1.1 or a signal to two-standard deviation noise ratio (SNR) of greater than or equal to about 2. Further, the one or more electrically conductive regions may comprise platinum, platinum black, carbon nanotube, carbon, or combinations thereof. Thus, the one or more electrically conductive regions can be used to detect neural chemicals, biochemicals, and/or other chemical agents.

In yet other aspects, the methods of the present teachings may include introducing the neural probe into the organism (e.g., implanting via surgical techniques) prior to the methods where the neural probe is used to electrically communicate with the target tissue in the organism. Such introducing can include at least one of the following implantation processes: pulling the neural probe, sewing the neural probe into, accelerating or injecting the neural probe, wrapping the neural probe around, or otherwise disposing and placing the neural probe adjacent to a target tissue of the organism. The introducing may include implanting the neural probe into a brain, or in certain other variations, may comprise implanting the neural probe near a spine, a peripheral nerve, vasculature, or an organ of the organism.

For example, a removable shuttle and/or a stiff dissolvable coating (such as crystallized PEG) may be used on the implantable probe (micro-component electrode) to assist with or facilitate the insertion of the micro-thread probe or an array of micro-thread probes into the organism. For example, a shuttle may be coated with a hydrophilic layer to assist in the separation of the shuttle and the probe after insertion to aid in the removal of the shuttle. Alternatively, a probe may be inserted into the tissue with high velocity (e.g., by injecting the probe with force). Further, in another aspect, it may be pulled or sewn into the target tissue (with a larger conventional shank or a needle) or wrapped around a nerve.

EXAMPLE 1

One, two, or three individual 7 μm diameter (Tensile Modulus 234 GPa) carbon fibers are mounted onto a NeuroNexus A16 print circuit board using silver epoxy (WPI; Sarasota, Fla.) and baked at 140° C. for 10 minutes. An approximately 800 nm thick parylene-N insulator layer is then coated via CVD, in a deposition chamber.

A reaction system for CVD polymerization comprises a sublimation zone, a pyrolysis zone, and a deposition zone. The CVD installation should provide (i) flexible control of polymerization parameters, (ii) monitoring capability to measure critical polymerization parameters in situ, and (iii) on line feedback capability for instant process control. CVD polymerization typically involves base pressures of around of $5 \times 10^{-5}$ bar and working pressures (i.e. the pressure during polymerization) of 0.05 to 0.4 mbar. The pressure control unit is located at the down-stream part of the equipment while the carrier gas inlet and flow control is located up-stream. This allows for controlling working pressure within a flexible range of gas flows and also prevents pressure fluctuations due to sublimation of the precursor.

One gram of paracyclophane is sublimed at 90-110° C. and 0.3 mbar and carried into the pyrolysis chamber by argon at a flow rate of 20 sccm. After pyrolysis at 670° C., the polymer is deposited on the substrate at 15° C. The deposition rate, according to the QCM, is 0.6-1.0 Å/s.

Parylene coated carbon fibers are then cut to a length of 0.3-0.5 cm. For PEDOT deposition, monomer 3,4-ethylenedioxythiophene (EDOT) (Bayer) is electrochemically polymerized and deposited onto the surface of the electrode sites together with the anions in the solution. Specifically, PEDOT/PSS is electropolymerized from a 0.1 M poly(sodium-p-styrenesulfonate) (PSS) (Acros Organics; Morris Plains, N.J.) aqueous solution with an EDOT concentration of 0.01 M under galvanostatic conditions. In galvanostatic mode, the current is varied from 50 to 500 pA.

Poly-ethylene glycol is immobilized onto the parylene surface by two different methods. Poly[(p-xylylene-4-methyl-2-bromoisobutyrate)-co-(p-xylylene)] is used as initiator for atom transfer radical polymerization (ATRP) because of its functional groups. After chemical vapor deposition of poly[(p-xylylene-4-methyl-2-bromoisobutyrate)-co-(p-xylylene)], microthread electrodes are incubated under inert conditions with degassed aqueous solution of oligo(ethylene glycol) methyl ether methacrylate, with CuBr/CuBr2/bpy as the catalyst. The polymerizations proceeded at room temperature for 4 hours. Microthread electrodes are thoroughly rinsed after the reaction.

In another technique, poly(p-xylylene carboxylic acid pentafluorophenolester-co-p-xylylene) is a polymer with an active ester group which can readily react with primary amine that is grafted to the functionalized coating. After chemical vapor deposition of poly(p-xylylene carboxylic acid pentafluorophenolester-co-p-xylylene), microthread electrodes are incubated in 10 mM mPEG-NH$_2$ (MW 10,000) PBS solution for 8 hours, followed by thorough rinses.

SEM imaging is carried out on a FEI Quanta 200 3D Focussed Ion Beam Workstation. Samples are sputter coated with gold prior to imaging.

The microthread probes are manually inserted into rat cerebral cortex to validate the insertion technique in a typical experimental preparation. Adult male Sprague-Dawley rats (Charles River Laboratories) weighing 300-350 g are prepared for cortical implants using previously established methods (Ludwig et al., 2006; Vetter et al., 2004). The animal is anesthetized with a mixture of 50 mg/mL ketamine and 5 mg/mL xylazine administered intraperitoneally with an initial dosage of 0.125 mL/100 g of body weight and regular updates of ketamine. The depth of anesthesia is regulated by monitoring heart rate and blood oxygen saturation. The animal is placed into a stereotaxic frame and a 2 mm by 2 mm craniotomy is made over the motor cortex. The dura is incised and resected. Sterile saline is used to keep the brain surface moist throughout the procedure. A stereotaxic frame mounted micromanipulator guided insertions of the microthread electrode 2 mm into the cortex. Due to the stiffness of the carbon fiber, a 2-5 mm long fiber did not need additional assistance in inserting into the cortex when inserted perpendicularly to the cortical surface using a stereotaxic guide.

In another aspect, a removable shuttle and/or a stiff dissolvable coating (such as crystallized PEG) may be used to assist in the introduction (e.g., insertion) of the microthread probe or an array of microthread probes into the organism. The shuttle may be coated with a hydrophilic layer to assist in the separation of the shuttle and the probe after insertion to aid in the removal of the shuttle. Alternatively, it may be inserted into the tissue with high velocity. Further, in another aspect, it may be pulled or sewn into the tissue (with a larger conventional shank or a needle) or wrapped around a nerve.

For in vivo neural recordings in the laboratory animals, electrophysiological data are acquired using a TDT RX5 Pentusa Recording System (Tucker-Davis Technologies, Alachua, Fla.). These neuronal signals are acquired through a head-stage buffer amplifier to avoid signal loss in data transmission. Signals are sequentially filtered by an antialiasing filter in the preamplifier, digitized at an approximate 25-kHz sampling rate, and digitally band-pass filtered from 2 to 5000 Hz. Wideband signals are acquired to capture both spiking and LFP activity. Signals are continuously recorded in segments ranging from 30 seconds to >10 minutes in duration.

Neural recording segments are analyzed offline to determine the number of neurons recorded, noise levels, and signal amplitudes using custom automated MatLab (Mathworks Inc., MA) software, as described in detail 84 and utilized elsewhere. As an overview, the wide-band recordings are filtered in software to isolate the spike data (300-5000 Hz) from the LFP data (1-100 Hz). To identify individual units, the threshold for the high-frequency data is established by using a window set at 3.5 standard deviations below the mean of the data. A 2.4-msec waveform is extracted from the data stream at each threshold crossing. To group isolated waveforms to a single neuronal unit, principal component analysis is then completed, and the resultant components are separated into individual clusters by using Fuzzy C-means clustering. Units with sufficiently clustered principal components are plotted, and the signal-to noise ratio is calculated as the peak-to-peak amplitude of the mean waveform of the cluster divided by six times the standard deviation of the remaining data stream after all waveforms had been removed.

Impedance spectroscopy measurements (EIS and CV measurements) are made using an Autolab potentiostat PGSTAT12 (Eco Chemie, Utrecht, the Netherlands) with associated frequency response analyzer and general purpose electrochemical system software (Brinkmann, Westbury, N.Y.), respectively. To obtain EIS and CV measurements, each probe is submerged in a phosphate buffered saline (PBS) solution of 137 mM sodium chloride, 2.7 mM potassium chloride, and 11.9 mM phosphate buffer with a stainless steel rod serving as the counter electrode and a standard Ag/AgCl probe as reference. Impedance measurements are taken between 10 Hz and 31 kHz at 25 mVrms. CV values are obtained by cycling three times from 0.8V to −0.6V at a sweep rate of 1 V/s and averaging the data. Charge storage capacity (CSC) of each site is calculated from the full area under the CV curve, scaled by the inverse of the scan rate. After implantation, a distant stainless steel (316-SS grade) bone screw is used as the reference and counter electrode.

In certain aspects, a microfabricated, thin polymer structure prepared in accordance with the principles of the present teachings can be attached to a larger, conventional shank such that the electrode site can be placed on the edge (FIGS. 5A-B and 6B). The micro-components of the present disclosure can be incorporated into parylene-substrate neural probes having a stiff penetrating shank (48 μm by 68 μm) supporting a thin lateral extension (5-μm thick and 100-μm wide). Probe structures fabricated with a sub-cellular dimension significantly reduced encapsulation while preserving healthy neurons around the thin edge (FIG. 7).

The most dramatic result is a significant decrease in encapsulation density around the lateral edge (L) relative to the shank (S). Encapsulation density at the lateral platform edge is almost ⅓$^{rd}$ the level around the device shank (129% and 425% increase in first 25 μm, respectively, P=0.00003, N=7 animals) (FIG. 7C). Significant decrease in neuronal loss is also observed. Neuronal loss is reduced from 30% to 48% in the first 25 μm from the interface (FIG. 3D). Qualitatively, a number of important results are also found. The ramified morphology of the microglia (O×42) indicated less activation, and astrocyte (GFAP) structure indicated only moderate hypertrophy (FIG. 7A). Most encouraging, microglia and other nonneuronal cells did not conform to the edge of the structure. The thin parylene structure (5 μm thick) elicited greatly reduced cellular encapsulation with no distinct capsular boundary.

Layer-by-Layer assembly of carbon nanotubes are used to form a core material of the inventive micro-components in certain variations of the present disclosure. Thus the core material optionally comprises a nanotube component made by a layer-by-layer assembly process employing a single-walled carbon nanotubes (SWNT) obtained from Carbon Nanotechnologies Inc. Since the LBL process relies on sequential adsorption of the oppositely charged components, the SWNT is non-covalently modified by the adsorption of a negatively charged polymer, poly(sodium-4-styrenesulfonate) (PSS, Sigma-Aldrich). The SWNT thin film is fabricated on a solid substrate such as silicon wafers or silicon probe mockups by sequentially dipping the substrate into dispersions of SWNT-PSS and polymer solutions. The individual layering step, adsorption of SWNT and polyelectrolyte monolayers, is intercepted by a rinsing and drying step to remove any excess solution and prevent cross contamination. The dipping time at each step of the layering process is varied to achieve best quality films but is not expected to exceed 20 min. Films of different thicknesses (or layers) are produced. Thick films (>100 layers) are used throughout this study for cellular, mechanical, electrical and electrochemical investigations. The progress of the film assembly is monitored by a variety of techniques, including UV-VIS, ellipsometry, atomic force microscopy (AFM) and scanning electron microscopy (SEM). Following LBL assembly, free standing films are achieved by detaching the SWNT films from the solid substrate by treatment with hydrofluoric acid (HF), a common etching solution. The as-prepared film on substrate is gently loaded into a bath of 5% aqueous HF solution until detachment of the film from the solid substrate is observed (few minutes). The detached film is rinsed in water and buffer solution to remove residual HF. Such a film is then optionally used a core material of the inventive micro-components.

EXAMPLE 2

In certain aspects, the present disclosure pertains to variations of the micro-component comprising platinum black coatings. By way of background, carbon fiber ultramicroelectrodes are known for in vivo dopamine sensing (as well as ascorbic acid and pH sensing) through amperometry (constant potential or cyclic voltammetry), and have also been used for electrophysiology recordings and enzymatic biosensing. Their small size makes them particularly attractive as a platform recording neural signals. In accordance with the present disclosure, carbon fibers have electrode-posited platinum black functionalization layers. In certain aspects, platinum black coatings offer several important advantages. First, platinum black increases the functional surface area, while having little to no change on the geometric area. Second, the platinum black coatings can be used to modulate electrode impedance, which can improve electrophysiology recordings. Third, platinum black can increase the charge capacity of the electrode for stimulation. Finally, as compared to bare carbon, platinum black has higher catalytic activity for the oxidation of hydrogen peroxide, which is a common detector molecule of enzymatic biosensors for choline, glutamate, glucose, and other neurochemicals. Carbon conductive regions (of the carbon fibers) as well as carbon nanotube or graphene-deposited conductive regions can also be used for chemical sensing.

An 800 nm insulation layer of parylene-n is deposited on a 7 μm diameter carbon fiber via chemical vapor deposition. Parylene-n is chosen as an alternative to the standard glass insulation to maintain flexibility of the fiber electrode. After parylene-n deposition, the end of the fiber is cut to expose a bare carbon tip (38.5 μm$^2$). Platinum black is electrochemically deposited on the exposed tip. The deposition is characterized and confirmed by impedance, cyclic voltammetry, and scanning electron microscopy. Using constant potential amperometry (700 mV vs. Ag/AgCl), robust sensitivity to hydrogen peroxide is demonstrated having applicability to peroxide-based biosensing mechanisms. Initial acute in vivo implantation in rat motor cortex showed the ability to record neuronal spikes with high fidelity. Such flexible carbon fiber electrodes having platinum black layers in the conductive surface regions provide a modular platform for neural recordings.

Details of insertion, such as tip shape, speed, and insertion location are important considerations for chronic neural interfaces. There is increasing evidence that the details of electrode insertion, such as electrode shape and insertion speed, may impact tissue damage. Details of probe insertion may also impact chemical trauma in tissue, as the implantation of microelectrodes punctures and tears neural vasculature. During insertion, the highly regulated blood brain barrier is compromised leading to plasma protein release into the surrounding parenchyma, resulting in adsorption onto the electrode, increased concentrations of extracellular serum proteins, ions, and other solutes, and deposition of plasma into the neuropi. Acutely, this damage can be observed as irregularities in neuronal spike activity, elevated levels of extracellular neurotransmitters and a net increase in extracellular water content. This vasogenic edema leads to increased brain tissue volume and intracranial pressure often associated with their impact on tissue damage and clinical outcome. This initial acute damage leads to the release of erythrocytes, clotting factors, and inflammatory factors from disrupted blood vessels, which facilitate recruitment of activated microglia and a broad region of astrocyte activation around the inserted probe. For example, albumin, the most abundant protein in blood plasma, is responsible, in part, for inducing glial cell activation and proliferation. Although stab wound studies show limited chronic tissue damage, plasma protein adsorption onto the electrode may perpetuate the tissue response in chronically implanted electrodes. While anti-biofouling coatings have issues with stability when implanted outside of the central nervous system (CNS), in certain aspects, it is theorized that the coatings on implantable devices in the CNS may only have to be stable and effective long enough for the cells to clean up the plasma exudates.

Furthermore, disrupting major arterioles during probe insertion can cause additional neuronal damage, by means of ischemia, through loss of perfusion to tissue below the disrupted region, which is typically where the recording sites are located. Drastically reducing feature size, stiffness, and applying a self-assembled monolayer anti-biofouling coating as provided by various aspects of the present inventive technology will likely reduce these acute insertion trauma effects.

Chronic in vivo electrophysiology is demonstrated in FIGS. 14A-14L. Initial chronic neural recording studies suggest that the biosensors prepared in accordance with certain aspects of the present teachings are stable over several weeks in the brain. For example, exemplary MTEs demonstrated high yield across animals for detecting single unit activity overtime (FIG. 14A—showing a percentage of active chronically implanted MTEs able to detect at least 1 single unit (dashed line) as a function of weeks post-implant (n=7)), which is comparable or better than the yield of conventional silicon devices or wire microelectrode arrays. The mean SNR of the largest discernable single unit detected by each MTE shows the stability of the chronic single unit recordings (FIG. 14B). During the initial inflammation period, the SNR decreases, then increases temporarily to a peak around one week before stabilizing. Tissue response to stab wounds subsides by four weeks suggesting stabilization of the tissue after surgery. For this reason, electrophysiological recordings are continued up to five weeks. By the second week the single units appear to stabilize as indicated by the decreased fluctuation and standard deviation. This is stabilization period is similar to previously reported studies. Deconstructing the mean SNR of the largest discernable single unit to the units' amplitude and the electrodes' noise floor shows that the fluctuations in SNR in the first two weeks is due to fluctuations largely in signal amplitude as opposed to fluctuations in noise floor (FIG. 14C). Examining individual electrodes for SNR or signal amplitude fluctuations further demonstrate the large variability observed in the first week after implantation, and stabilization after the second week (FIG. 14D). FIGS. 14E-14F demonstrate two examples of over 5 weeks of chronic recordings from two different animals. These initial chronic recording studies demonstrate that the inventive biosensors remain intact in the brain over moderate lengths of time, without any electrophysiological evidence of signal degradation. They also have extremely high yield of unit recordings compared to conventional Silicon-on-Anything (SOA) probes.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. An implantable micro-component electrode comprising:
   a core consisting of an electrically conductive core material;
   one or more electrically conductive regions disposed directly on the surface of the electrically conductive core material comprising an electrically conductive biocompatible coating;
   an electrically non-conductive biocompatible coating disposed directly on regions of the surface of the electrically conductive core material where the one or more electrically conductive regions are absent; and
   a layer comprising a biofunctional agent disposed directly on the electrically non-conductive biocompatible coating, the biofunctional agent being poly(ethylene glycol) (PEG) or poly(ethylene glycol methacrylate) (PEGMA),
   wherein the micro-component electrode has at least one dimension of less than or equal to about 10 μm.

2. An implantable micro-component electrode of claim 1, wherein the electrically conductive core material that has an elastic tensile modulus of greater than or equal to about 200 GPa and a nominal value of stiffness of greater than or equal to about 5 GN/μm and the electrically non-conductive biocompatible coating has a thickness of less than 1 μm.

3. The implantable micro-component electrode of claim 1, wherein the electrically conductive core comprises carbon.

4. The implantable micro-component electrode of claim 3, wherein the electrically conductive core is selected from the group of materials of carbon fibers, composites comprising single-walled carbon nanotubes, composites comprising multi-walled carbon nanotubes, graphene, and combinations thereof.

5. The implantable micro-component electrode of claim 1, wherein the electrically conductive core comprises a metal selected from the group consisting of: gold, platinum, tungsten, steel, iridium, or combinations thereof.

6. The implantable micro-component electrode of claim 1, wherein the electrically conductive coating comprises a conductive biocompatible material selected from the group consisting of: poly(3,4-ethylene dioxythiophene) (PEDOT) with a poly(4-styrenesulfonate) (PSS) counter ions, polypyrrole, platinum, iridium oxide, carbon nanotubes, graphene, and combinations thereof.

7. The implantable micro-component electrode of claim 1, wherein the electrically non-conductive biocompatible coating comprises a parylene polymer or a parylene polymer derivative.

8. The implantable micro-component electrode of claim 1, wherein at least one of the electrically conductive core material or the electrically non-conductive biocompatible coating are patterned, shaped, and/or etched.

9. An implantable neural probe medical device comprising one or more of the micro-component electrode of claim 1.

10. A micro-component electrode for an implantable medical device comprising:
    a core consisting of an electrically conductive core material comprising carbon and having a diameter of less than or equal to about 10 μm;
    one or more electrically conductive regions disposed directly on the surface of the electrically conductive core material comprising an electrically conductive polymeric coating; and
    an electrically non-conductive polymeric coating disposed directly on regions of the surface of the electrically conductive core material where the one or more electrically conductive regions are absent, wherein the electrically non-conductive coating comprises a parylene polymer or a parylene polymer derivative.

11. The micro-component electrode of claim 10, wherein the electrically conductive core is selected from the group of materials of carbon fibers, composites comprising single-walled carbon nanotubes, composites comprising multi-walled carbon nanotubes, graphene, and combinations thereof.

12. The micro-component electrode of claim 10, wherein the electrically conductive polymeric coating comprises a conductive biocompatible material selected from the group consisting of: poly(3,4-ethylene dioxythiophene) (PEDOT)

with a poly(4-styrenesulfonate) (PSS) counter ion, polypyrrole, carbon nanotubes, graphene, and combinations thereof.

13. The micro-component electrode of claim 10, wherein the electrically non-conductive biocompatible coating further comprises one or more biofunctional agents.

14. An implantable neural probe medical device comprising one or more of the micro-component electrodes of claim 10.

15. A method of monitoring, sensing, or stimulating neural activity in an organism, the method comprising:
electrically communicating with a neural probe implanted into a brain of the organism, the neural probe having a cross-sectional area of less than or equal to about 2,000 µm² and comprising at least one micro-component electrode comprising a core consisting of an electrically conductive core material having a surface with one or more electrically conductive regions disposed directly on the surface of the electrically conductive core material comprising an electrically conductive polymeric coating; an electrically non-conductive polymeric coating disposed directly on regions of the surface of the electrically conductive core material corresponding to locations where the one or more electrically conductive regions are absent; and a layer comprising a biofunctional agent disposed directly on the electrically non-conductive biocompatible coating, the biofunctional agent being poly(ethylene glycol) (PEG) or poly(ethylene glycol methacrylate) (PEGMA), wherein the micro-component electrode has at least one dimension less than or equal to about 10 µm.

16. The method of claim 15, wherein the neural probe is able to detect at least one neuronal spike with a signal to peak-to-peak noise ratio (SNR) of greater than or equal to about 1.1 or a signal to two-standard deviation noise ratio (SNR) of greater than or equal to about 2.

17. The method of claim 15, further comprising introducing the neural probe into the organism prior to said electrically communicating.

18. The method of claim 17, wherein the introducing comprises implanting the neural probe near a spine, a peripheral nerve, vasculature, or an organ of the organism.

19. The implantable micro-component electrode of claim 1, wherein the layer comprising a biofunctional agent comprises an active biomolecule selected from the group consisting of neural cell adhesion molecule (NCAM), brain-derived neurotrophic factor (BDNF), glycosaminoglycans, and combinations thereof.

20. The implantable micro-component electrode of claim 13, wherein the one or more biofunctional agents is at least one of poly(ethylene glycol) (PEG) and poly(ethylene glycol methacrylate) (PEGMA).

21. The implantable micro-component electrode of claim 10, wherein the electrically non-conductive polymeric coating further comprises an active biomolecule selected from the group consisting of neural cell adhesion molecule (NCAM), brain-derived neurotrophic factor (BDNF), glycosaminoglycans, and combinations thereof.

22. The implantable micro-component electrode of claim 1, wherein the electrically conductive core material is a carbon fiber.

* * * * *